United States Patent [19]

Frank et al.

[11] Patent Number: 5,042,499
[45] Date of Patent: Aug. 27, 1991

[54] NONINVASIVE ELECTROCARDIOGRAPHIC METHOD OF REAL TIME SIGNAL PROCESSING FOR OBTAINING AND DISPLAYING INSTANTANEOUS FETAL HEART RATE AND FETAL HEART RATE BEAT-TO-BEAT VARIABILITY

[76] Inventors: Thomas H. Frank, 1703 Peartree La., Crofton, Md. 21114; Richard K. Gibbs, 9477 Muirkirk Rd., Apt. No. 102, Laurel, Md. 20748; Robert L. Wells, 1223 Scots Manor Ct., Apt. E, Odenton, Md. 21113

[21] Appl. No.: 561,575

[22] Filed: Aug. 2, 1990

Related U.S. Application Data

[63] Continuation of Ser. No. 251,458, Sep. 30, 1988, abandoned.

[51] Int. Cl.⁵ ............................................ A61B 5/0448
[52] U.S. Cl. ...................................... 128/698; 128/696
[58] Field of Search ............... 128/696, 698, 688, 695, 128/706, 710; 364/413.06

[56] References Cited

U.S. PATENT DOCUMENTS

| | | | |
|---|---|---|---|
| 3,572,317 | 3/1971 | Wade | 128/696 |
| 3,599,628 | 8/1971 | Abbenante et al. | 128/698 |
| 3,811,428 | 5/1974 | Van Horn et al. | 128/2.06 F |
| 3,916,878 | 11/1975 | Courtin et al. | 128/2.06 F |
| 4,018,219 | 4/1977 | Hojaiban | 128/706 |
| 4,211,237 | 7/1980 | Nagel | 128/698 |
| 4,256,118 | 3/1981 | Nagel | 128/698 |
| 4,513,295 | 4/1985 | Jones et al. | 128/698 |
| 4,519,396 | 5/1985 | Epstein et al. | 128/698 |
| 4,781,200 | 11/1988 | Baker | 128/706 |
| 4,803,996 | 2/1989 | Peel et al. | 128/696 |

OTHER PUBLICATIONS

Datascope Catalog, "Advanced Monitors for Anesthesia", May 1984.
Earl R. Ferrara and Bernard Widrow, "Fetal Electrocardiogram Enhancement by Time-Sequenced Adaptive Filtering", IEEE Transactions on Biomedical Engineering, vol. BME-29, No. 6, Jun. 1982, pp. 458-460.

*Primary Examiner*—William E. Kamm
*Assistant Examiner*—Scott M. Getzow
*Attorney, Agent, or Firm*—James Creighton Wray

[57] ABSTRACT

A fetal heart rate monitor monitors weak fetal electrocardiogram signals in the presence of strong interfering maternal ECG complexes, general random background muscle noise, and 60 Hz power line noise. An electrocardiographic adaptive cancellation process to cancel the maternal ECG component from an abdominal ECG signal recorded from a pregnant subject's abdomen signal is processed using computer software. A set of easily movable maternal abdominal and thoracic ECG electrodes is used. An operator views the ECG data in an oscilloscope and optimally places the set of thoracic electrodes to adaptively cancel the maternal ECG signal from the signal separately derived from a movable abdominal electrocardiographic lead. The invention noninvasively obtains from the abdomen of a pregnant subject the fetal ECG signal, fetal heart rate, and accurate beat-to-beat fetal heart rate variability. Computer software provides cancellation of the maternal ECG component derived from a maternal abdominal ECG lead using a separate set of maternal thoracic ECG leads. A starting fetal ECG signal is obtained from an electrocardiographic digital signal processing normalized correlation automatic start-up procedure. Ensuing fetal ECG complexes are matched with the starting complex for detecting ensuing ECG signals. Fetal heart rate and FHR variability are accurately and reliably measured and reported from the signals in an instantaneous or beat-to-beat fashion.

68 Claims, 10 Drawing Sheets

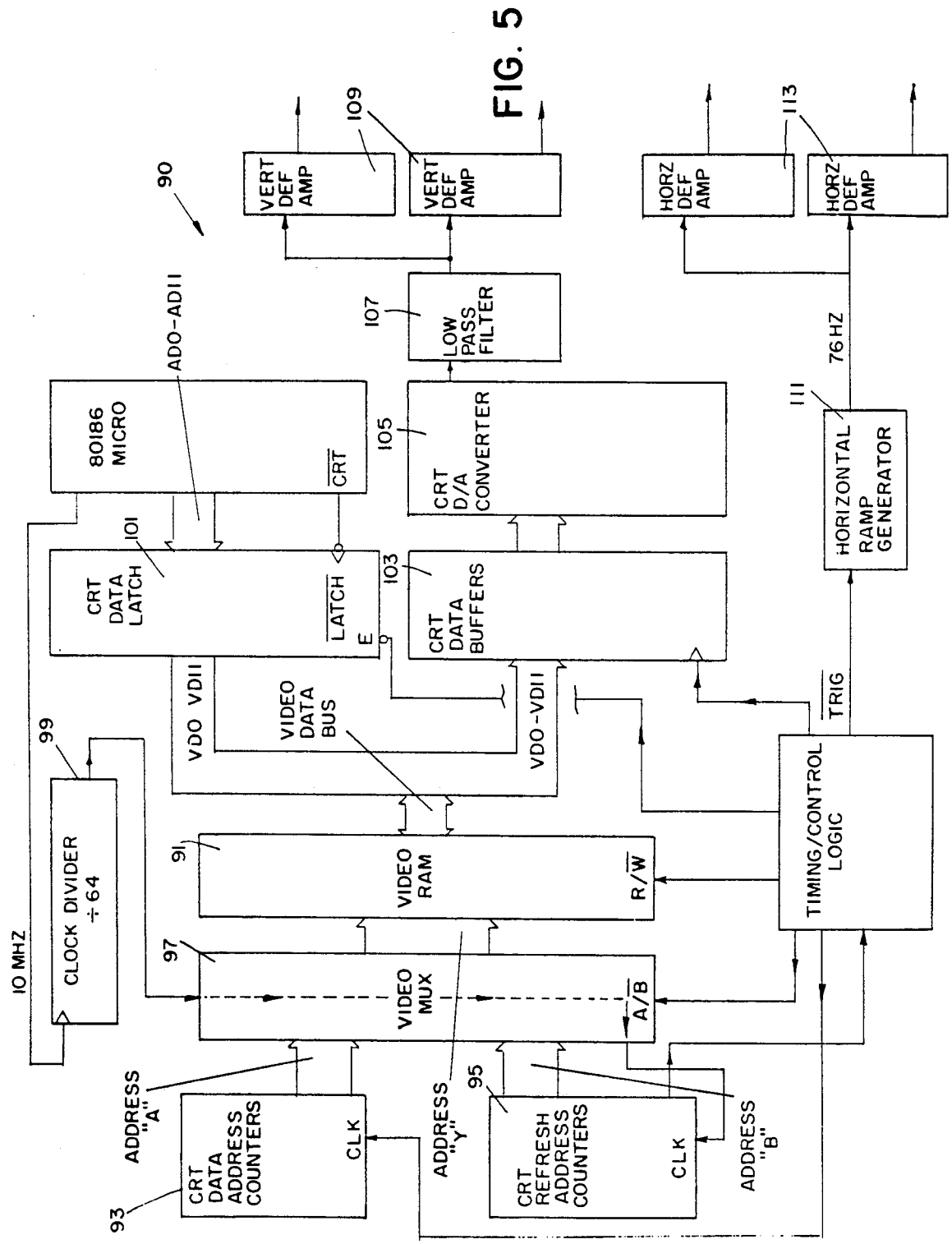

NONINVASIVE ELECTROCARDIOGRAPHIC METHOD OF REAL TIME SIGNAL PROCESSING FOR OBTAINING AND DISPLAYING INSTANTANEOUS FETAL HEART RATE AND FETAL HEART RATE BEAT-TO-BEAT VARIABILITY,

This application is continuation of application Ser. No. 251,458, filed Sept. 30, 1988, now abandoned.

BACKGROUND OF THE INVENTION

1. Field of Invention

This invention relates to monitoring and processing weak biological signals in the presence of noise and interference. The invention is particularly applicable to the accurate noninvasive measurement of instantaneous fetal heart rate and fetal heart rate variability and a continuous tracing of the fetal electrocardiogram. The invention also provides the multiplexing and converting of analog signals, storing digital signals, repetitively digitally sampling of a group of signals in a burst of time, and sending the digital samples to a microprocessor for digital signal processing.

2. Description of the Prior Art

A clinical need has developed to monitor the instantaneous fetal heart rate (FHR) and changes in the heart rate from one beat to the next, i.e., beat-to-beat FHR variability. A fetal heart rate (FHR) monitor should process this information and ideally display FHR, FHR variability and uterine activity (UA) continuously in a real-time fashion.

The fetal heart rate is universally considered to provide valuable information for monitoring the status of the fetus both during labor and during the third trimester of pregnancy. During the past fifteen years it has become generally accepted that the instantaneous fetal heart rate and changes in the heart rate from one beat to the next (beat-to-beat variability) provide important clinical information. The variability is altered by the sympathetic and parasympathetic nervous systems under further regulation by cerebral centers and reflexes. Clinically there is general agreement that a fairly large amount of variability is an indication of fetal well being and that the absence of variability is an ominous sign both before and during labor. Fetal heart rate can be measured most accurately by electrocardiography using an electrode attached to the fetal scalp. This technique is invasive and can be used only at labor and delivery because it involves rupture of the amniotic membranes, the dilation of the cervix and clear identification of the fetal presenting part.

Recent noninvasive methodologies applied to fetal heart monitoring include Doppler ultrasound with autocorrelation, phonocardiography, and other electrocardiographic techniques. None of these noninvasive techniques has yet been developed to the state where it can consistently monitor instantaneous fetal heart rate and fetal heart rate beat-to-beat variability before labor and delivery in a reliable and accurate manner.

SUMMARY OF THE INVENTION

A noninvasive fetal heart rate monitor based on an electrocardiographic adaptive processor provides real-time continuous tracings of the fetal ECG, fetal heart rate (FHR), and FHR variability. This invention is capable of obtaining accurate records of beat-to-beat FHR variability noninvasively using standard paste-on ECG electrodes to collect both maternal thoracic and abdominal ECG signals. No invasive procedures are required; no ultrasonic energy is needed; amniotic membranes do not need to be ruptured; and the cervix does not need to be dilated using this technique.

The primary importance of this invention is that an accurate measure of FHR beat-to-beat variability was not previously available by any noninvasive means. The object of the present noninvasive diagnostic instrumentation technique is to monitor the fetal electrocardiogram (FECG), fetal heart rate (FHR) and FHR variability and thus enable the evaluation of fetal well-being throughout gestation. Beat-to-beat FHR variability, accurately and noninvasively measured at labor and delivery, is likely to be a more important predictor of fetal well-being at birth than the present cumbersome protocol of obtaining invasive, intermittent measurements of fetal scalp blood pH during delivery. In addition, the noninvasive monitoring of the fetal electrocardiogram during early gestation should provide insight into the development of birth defects including heart and vascular diseases.

Tracings of the fetal QRS complex, instantaneous FHR, and short-term beat-to-beat FHR variability have been obtained in real-time. Fetal R-R intervals are determined at an accuracy of 99.6% in the worst case for a nominal FHR of 120 beats/minute Clinical tests demonstrate that a reliable measure of beat-to-beat variability can be made noninvasively in a continuous fashion. The clinical acceptance and utilization of a new instrumentation technique depends as much on the simplicity of using the technique as well as the incremental gain in the diagnostic information it provides. This invention demonstrates for the first time that adaptive ECG cancellation techniques can provide real gains in noninvasive fetal heart rate monitoring.

The initial design and programming of the maternal ECG cancellation concept was implemented using a microcomputer with disc storage. After the data collection part of the process was demonstrated to be capable of noninvasively obtaining fetal ECG signals, the data processing portion of the entire process was executed on the microcomputer providing the capability of processing fetal ECG data off-line (not in real-time). That is, maternal and thoracic ECG data initially stored on computer disc were subsequently used to test the adaptive techniques to cancel the strong interfering maternal ECG.

In a controlled laboratory environment, adaptive cancellation of the maternal ECG signal may be complete in the sense of totally eliminating the abdominal component of the maternal ECG signal to reveal a continuous tracing of the fetal ECG signal even during the maternal and fetal ECG coincidence or near-coincidence in time.

The initial data acquisition portion of the system used to collect the fetal ECG data for later off-line processing was awkward and cumbersome to deal with at best in the Labor and Delivery Suite. This was, in itself, one of the motivations for the development of a small, totally integrated, and truly portable real-time electrocardiographic adaptive processor instrumentation system. In addition, in the labor and delivery suite or antepartum testing facility, the environment is dynamic. Dependent upon fetal lie and position, initial thoracic and abdominal lead placement, and the many practical considerations of data collection in a hospital environment, the fetal ECG signal itself can be quite small or completely lacking in the raw data obtained from maternal abdominal ECG lead locations. Also, the maternal ECG signal cancellation can later be found to be incomplete using the pre-established thoracic lead locations in the subsequent off-line processing. Therefore, this hybrid on-line data collection and off-line data processing implementation was not always effective. The present stand-alone integrated monitor deals with these real problems, provides for operator interaction, and produces processed results immediately in real-time.

In reducing the fetal monitor to practice, problems have been solved in three critical areas. First, a data collection system has been implemented to collect multiple channels of ECG data in bursts. Second, adaptive cancellation algorithms have been optimized to execute in real-time and to effectively cancel the strong maternal abdominal ECG interference to provide a record of the fetal ECG signal. Third, the microprocessor based fetal heart rate monitor, utilizing the electrocardiographic adaptive processor system, has been configured to provide a real-time instrumentation system yielding a continuous fetal ECG record and to enhance this fetal ECG signal to provide an accurate record of instantaneous FHR and FHR beat-to-beat variability. In addition, the adaptive cancellation process has been permanently embedded in an electrically programmable read only memory (EPROM) hardware device to become firmware.

The adaptive cancellation process is a sequence of operations to remove the maternal abdominal projection of several thoracic leads from a given maternal abdominal lead producing a clear fetal electrocardiogram. That sequence consists of three steps. First, computation of a basis set of vectors are obtained by the Gram-Schmidt orthogonalization process. Second, a set of adaptive cancellation weights are computed. Lastly, subtraction adaptively removes the abdominal projection of the maternal ECG component leaving the fetal ECG signal intact.

The present effective system does not take algorithmic short cuts aimed at reducing the number of arithmetical computations. There are variations in the maternal and fetal ECG signals with time and, thus, variations in the set of basis vectors that should be used to represent those signals. While we have found that by maintaining a single set of "typical" basis vectors, the computer time required to constantly update them is saved. However, in almost all cases, maintaining a single set of "typical" basis vectors results in a poorer maternal ECG cancellation. The effectiveness of this maternal ECG adaptive cancellation process has been optimized by varying a number of parameters that influence electrocardiographic cancellations: namely, cancellation time window duration, modifying ECG data sampling rate, and modifying ECG lead placement.

Increasing the duration of the maternal ECG cancellation time window to extend well beyond the entire ECG complex improves cancellation performance. The optimum cancellation time window duration is as large as is computationally possible. A window duration of 500 msec has been found to be quite adequate for almost all cases. Smaller cancellation periods, as small as 150 msec or 300 msec, may result in adequate cancellation performance, but depend heavily upon the quality of the raw data. Surprisingly, we have found, that cancellation windows that are contiguous in time, without gaps, and therefore chosen independently of the time position of the maternal complex are very effective in maternal ECG cancellation. Thus, all data points in the abdominal ECG lead are canceled, whether or not they contain any or all portions of the maternal ECG, allowing artifacts common to the abdominal lead and some or all of the thoracic leads to be removed by the cancellation process as well as the entire maternal ECG (i.e., P, QRS, and T waves) wave form.

Increasing the electrocardiographic sampling rate to 500 Hz improves maternal ECG cancellation performance by providing greater time resolution in the ECG signal representation. Sampling rates as low as 150 samples/second and as high as 1000 samples/sec have been examined. Optimum data cancellation was determined to be 500 samples/sec/channels. Rates lower than 500 samples/sec tend to result in poor cancellation and data collection rates greater than 500 samples/sec do not yield significant improvements in future processing. It is important to note here that, as the sampling rate increases, the amount of data and hence the real-time processing requirements, increases proportionately. Data collection from all ECG inputs is completed in a burst format within a time interval of about 120 usec. Hence, the data from all ECG inputs is sampled virtually simultaneously from all inputs every 2 msec.

Increasing the sampling rate, avoiding computational short cuts, and increasing the maternal cancellation time window duration requires that more data be processed in the same period of time to achieve real-time performance. Using a number of timing measurement procedures, the actual real-time execution speeds of the software modules have been determined. The processor is fast enough to execute all of the adaptive algorithms in real-time. The percentage of the 10 MHz 80186 processor time required to execute each of the software modules is tabulated below:

| Timing Measures for Real-Time Electrocardiographic Adaptive Processor | | |
|---|---|---|
| | Processing Time (%) | |
| Software Module | Estimated | Measured |
| 1. Data Collection I/O Control and Interrupt Service Routines | 5.0 | 12.0 |
| 2. Adaptive Maternal ECG Cancellation | 12.5 | 16.0 |
| 3. Fetal ECG Matched Filter | 14.6 | 14.0 |
| 4. Square Function | — | 6.0 |
| 5. Fetal Detections, Instantaneous Fetal FHR & Variability Calculations | — | 1.0 |
| 6. Reserve | 67.9 | 51.0 |
| | 100.0% | 100.0% |

As the table indicates, the percentage of the 10 MHz 80186 processor utilization to achieve real-time performance is only 49.0%.

Cancellation of the abdominal maternal ECG signal, when optimized as described, consistently reveals hidden fetal QRS complexes that were embedded in the maternal abdominal ECG signal. This allows for the complete enumeration of the fetal complexes and subsequent accurate computation of instantaneous FHR and FHR beat-to-beat variability.

The invention is embodied in the Perinatronics Model FHR 186 fetal heart rate monitor. This is an electrocardiographic adaptive processor (EAP) which can adaptively cancel in real-time the maternal electrocardiogram from an abdominal signal to provide an accurate record of fetal heart rate and beat-to-beat variability.

It utilizes an 80186 microprocessor running at 10 MHz to perform the cancellation algorithm. It incorporates an 8-channel multiplexer and 12-bit, 12 microsecond successive approximation analog-to-digital converter. Integrated with the microprocessor system are a 3-inch cathode ray tube and a 4.5-inch high-resolution thermal array printer to provide an immediate view and copy of fetal ECG or the fetal heart rate and beat-to-beat variability. This monitor provides a noninvasive real-time method of measuring instantaneous fetal heart rate, beat-to-beat variability, and fetal ECG. A photograph of the FHR 186 is shown in FIG. 16.

BRIEF DESCRIPTION OF THE DRAWINGS

FIG. 5: Cathode Ray Tube Block Diagram showing generation of signals to horizontal and vertical deflection plates.

DESCRIPTION OF THE PREFERRED EMBODIMENT

Figure 1:
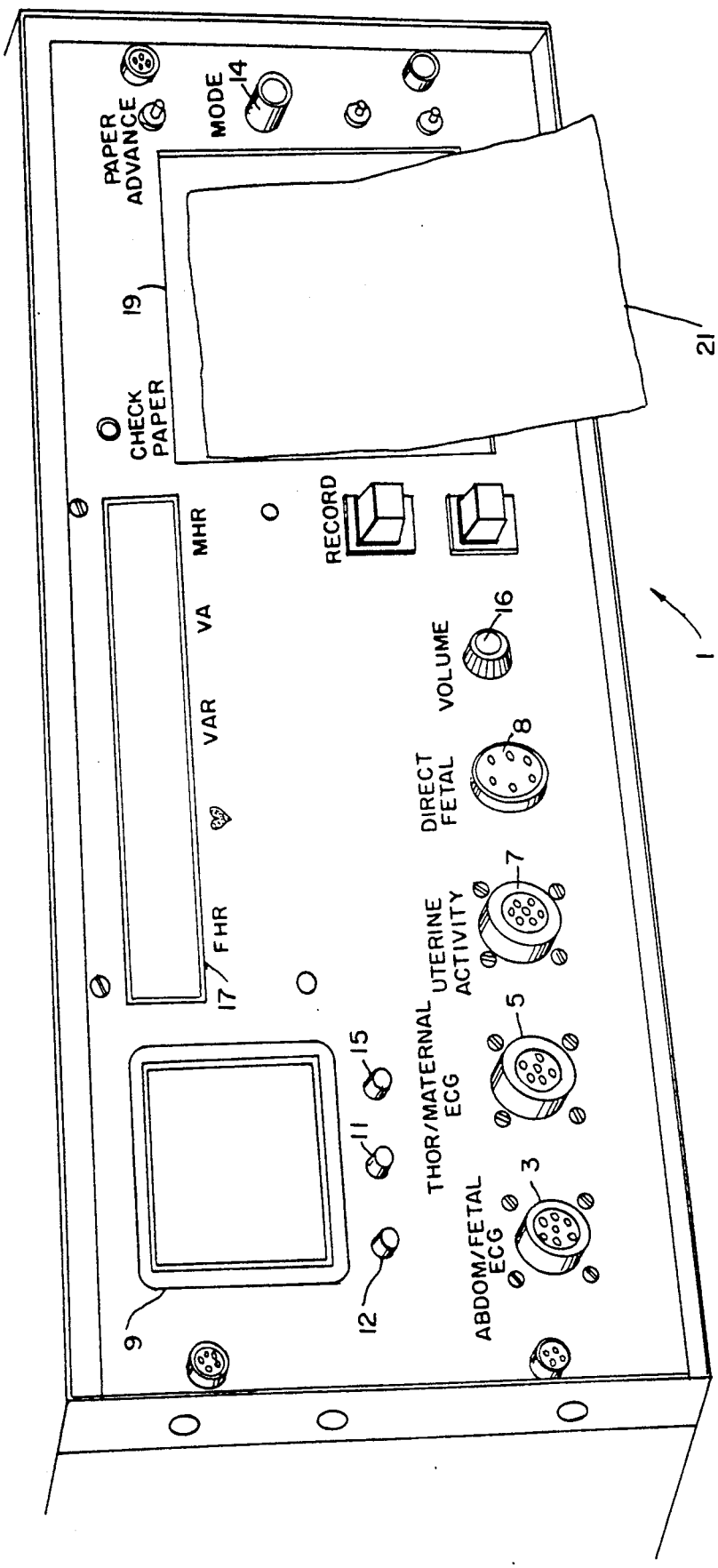
FIG. 1: Perinatronics Fetal Heart Rate Monitor Model FHR 186 using the electrocardiographic adaptive processor.

The Perinatronics FHR 186 monitor 1 shown in FIG. 1 provides a flexible instrument to adaptively cancel, in real-time, the maternal electrocardiogram component from maternal abdominal leads, 2 (FIG. 2) connected to input 3 (FIG. 1) using thoracic electrocardiographic leads connected to input 5 to provide a continuous tracing of the fetal ECG complex, FHR, and FHR variability.

A uterine activity input 7 may be connected to a uterine probe. A direct fetal input 8 is also provided. A CRT screen 9 displays maternal abdominal or fetal ECG signals as controlled by switch 11. Freeze/scan switch 13 permits stopping and holding an image on screen 9. Start button 15 restarts the matched filter start up procedure. All control knobs may be push buttons except the chart recorder mode control switch 14 and the FHR detection volume control knob 16.

A seven-segment display 17 concurrently displays fetal heart rate, variability, uterine activity, if used, and maternal heart rate. A printer 19 provides a continuous printout 21 as later described.

The heart of the instrument is its general purpose microprocessor. The 80186 microprocessor running at 10 MHz available from Intel is preferred. This choice is based primarily on the processor's speed, high integration, and reasonable cost. It integrates many of the peripheral chips necessary to support a small system of this type. This keeps complexity down, simplifies design and saves space. The system incorporates an 8-channel multiplexer and a 12-bit, 12 usec successive approximation analog-to-digital converter, which samples eight channels at 500 samples/sec/channel.

The adaptive processing algorithms per se are programmed in modules of highly efficient macro assembly language computer code and stored in less than 16K bytes of EPROM using 64K bytes of RAM memory to buffer data and hold all processing variables. The modules include interrupt service routines to collect four channels of ECG data and control I/O devices, adaptive maternal ECG cancellation firmware modules, fetal ECG matched filter signal enhancement and subsequent detection firmware modules, and instantaneous FHR calculations.

Integrated with the microprocessor system is a three-inch cathode ray tube 9 used to view the effectiveness of the cancellation process and the presence of the fetal ECG signal in the abdominal data. A 4.6 -inch, high-resolution thermal array printer 19 provides immediate views and copies 21 of fetal ECG tracings or FHR and FHR variability tracings.

Figure 8:
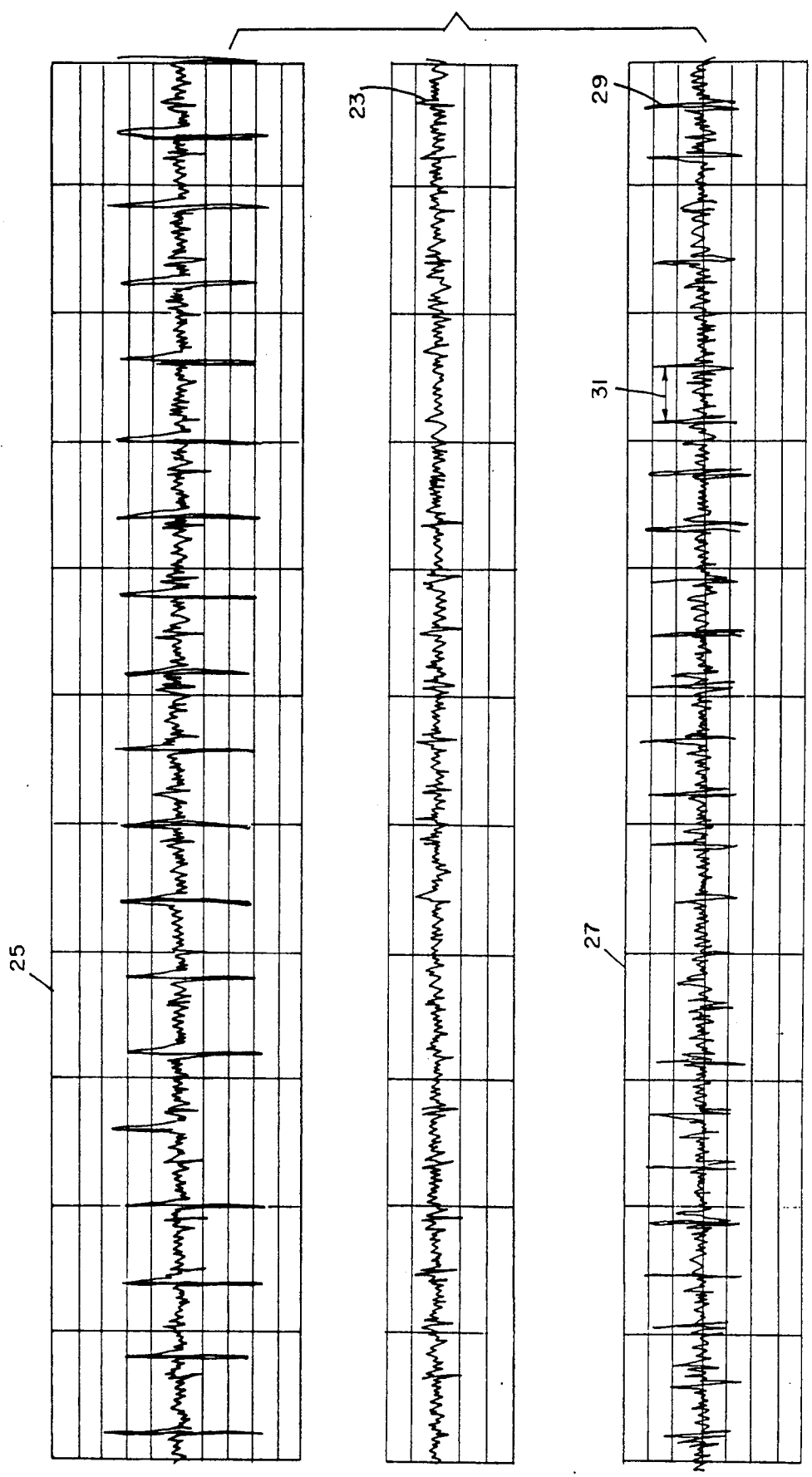
FIG. 8: Voltage-time graphs (@25 mm/sec) illustrating: a) (upper tracing) a portion of the data as collected at the output of the analog front end of Channel 4 displaying the data obtained from a noninvasive abdominal ECG lead consisting of the larger interfering maternal abdominal ECG data with smaller and often coincident fetal ECG data and background electromyographic noise; and b) (second tracing) a portion of the processed signal time aligned with the upper tracing obtained following the cancellation procedure illustrating the complete cancellation of each and every maternal ECG complex to below the level of the fetal ECG complexes, even when the maternal and fetal ECG complexes are nearly or completely time coincident; c) (lower tracings) a portion of the processed signal time aligned with the upper tracing obtained following the matched filter (MFLTR) procedure illustrating the enhanced signal level to background noise level of fetal ECG complexes.

A sample tracing displaying the extraction of the fetal ECG from coincident maternal ECG complexes is shown in FIG. 8. FIG. 8 shows portions of a fetal ECG tracing displaying the extraction of the fetal FECG signal 23 (2nd tracing) from noninvasive maternal abdominal ECG data 25 with coincident fetal and interfering maternal ECG complexes (upper tracing). In FIG. 8, three channels of ECG data are plotted at standard ECG paper speed of 25 mm/sec. The upper tracing 25 is the noninvasive maternal abdominal ECG signal showing the larger maternal ECG interference, a smaller fetal ECG signal and the background noise level. The second tracing, which is time coincident with the upper one, displays the fetal ECG signal 23 following adaptive cancellation of the maternal ECG. The lower tracing displays enhanced fetal signals 27 using the matched filter procedure to improve the fetal signal-to-noise ratio. All of the fetal QRS complexes 29 are visible here s that R-R intervals 31 can subsequently be computed to provide an instantaneous measure of FHR and R-R interval differences can be used to provide beat-to-beat FHR variability.

Figure 11:
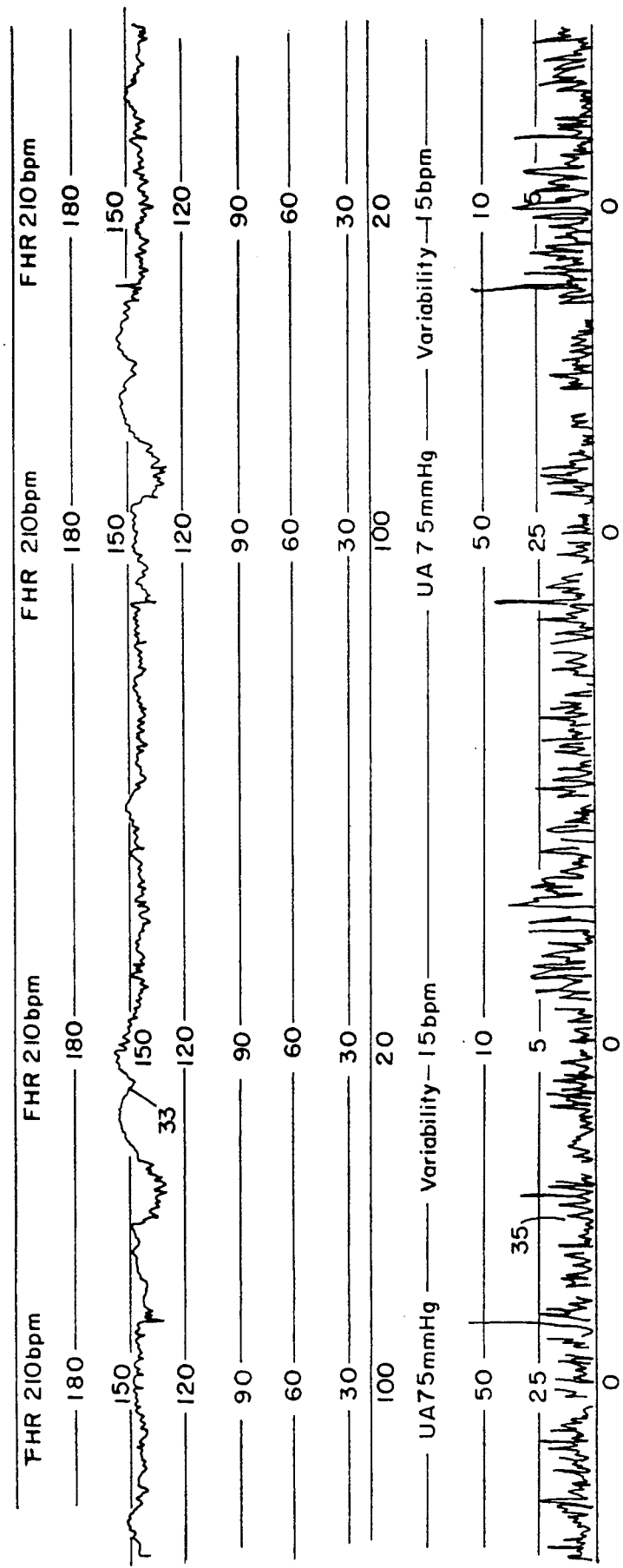
FIG. 11: Display of fetal heart rate and fetal heart rate variability. The upper tracing displays the computation of instantaneous fetal heart rate at the conventional scaling of 30 bpm/cm and plotted at a speed of 3 cm/sec. The lower tracing displays the beat-to-beat FHR variability on a scale of 0 to 20 bpm. Uterine activity can be superimposed on the lower tracing on a scale of 0 to 100 mm Hg.

FIG. 11 displays instantaneous fetal heart rate 33 and beat-to-beat FHR variability 35 on a single plot at standard FHR paper speed of 3 cm/min. The upper tracing in FIG. 11 provides instantaneous FHR plotted from 30 to 210 bpm. At the average rate of 120 beats/minute, the plot displays 5 minutes of data or approximately 600 R-R intervals in 15 cm. The lower tracing displays beat-to-beat variability on an expanded scale of 0 to 20 bpm. The record has not been cosmetically altered, thus some artifacts may be present in the record. Therefore, we have been able to achieve an accurate, non-averaged, measure of beat-to-beat FHR variability noninvasively. Other noninvasive FHR monitors display a cosmetically acceptable FHR record by averaging the data, however, this is not an accurate measure of beat-to-beat variability. It is important, therefore, that all instrumentation used for FHR recording using noninvasive techniques, such as Doppler ultrasound or indirect fetal electrocardiography, clearly distinguish between actual and supplied data. This is especially true in evaluation of short-term beat-to-beat FHR variability.

Figure 2:
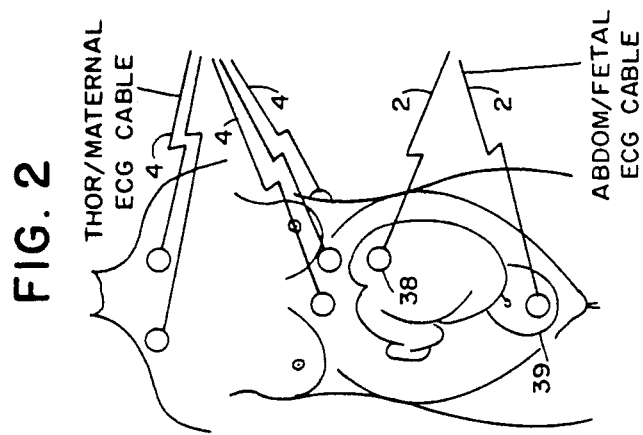
FIG. 2: Anatomical drawing of pregnant maternal abdomen and thorax depicting preferred location of thorax/maternal ECG leads and abdominal/fetal ECG leads for fetal heart rate monitoring.

The procedure for using the invention to obtain a continuous tracing of the fetal heart rate and fetal heart rate variability or a tracing of the fetal ECG signal is described below. The procedure involves placing maternal and thoracic ECG electrodes 38, 39 (FIG. 2) on the pregnant maternal abdomen and thorax, adjusting their positions, if needed, to obtain the best signals while observing the CRT display 9 (FIG. 1), depressing the monitor restart button 15 (FIG. 1), as necessary, after moving the electrodes and then allowing the monitor to automatically select a good starting fetal ECG complex and subsequently providing a continuous tracing of the FHR, FHR beat-to-beat variability or fetal ECG signal on chart recorder 19 (FIG. 2).

First, the power to the monitor is turned on by actuating a toggle switch on the rear of the monitor and the seven segment LED 17 will display "HELLO", indicating that the monitor has passed a built-in-test and is ready. After a pause of a few seconds the uterine activity LED 17 will display a "1" indicating that the first set of electrodes the thoracic electrodes 39, should be attached.

For ease of application all electrodes are color coded to enable them to be placed at their proper anatomical locations. A thoracic cable is connected to the monitor at thoracic/maternal plug 5 (FIG. 1) and colored alligator clips are used to connect thoracic electrodes 39 (FIG. 2) to the pregnant women as follows:

Green Thoracic Electrode 39: This electrode, which provides thoracic signal No. 1, is placed on the right clavicle toward the right shoulder.

Black Thoracic Electrode 39: This electrode, which provides thoracic signal No. 2, is placed on the left clavicle toward the left shoulder.

White Thoracic Electrode 39: This electrode, which provides thoracic signal No. 3, is placed on the left mid-axillary line at the height of the sternal notch.

Red Thoracic Electrode 39: This electrode, which is common to thoracic signal numbers one, two, and three, is placed immediately below the sternal notch and probably on the fundus of the uterus on a subject close to delivery of her baby.

Brown Thoracic Electrode: This is the reference electrode for all thoracic and abdominal electrodes. There is no specific preferred position for this electrode, however, it is usually placed below the red electrode on the maternal abdomen.

Following the placement of the thoracic electrodes 39 the monitor should indicate the number "2" on the uterine activity LED display 17. This indicates that the second set of electrodes, the abdominal electrodes 38, should be attached. An abdominal electrode cable is connected to the monitor at abdominal/fetal plug 3 (FIG. 1) and colored alligator clips are used to connect abdominal electrodes 38 to the pregnant women as follows:

Yellow Abdominal Electrode 38: With the usual fetal position of head down, this electrode is placed on the maternal abdomen over the position of the fetal head using Leapold's maneuvers to palpate the pregnant maternal abdomen or by using ultrasonic imaging, if necessary, to determine the position of the fetal head. This electrode is usually placed on the mid-line of the the abdomen just above the pubic hair line on the pubic symthysis.

Black Abdominal Electrode 38: This electrode is placed over the fetal buttock, again by the use of Leapold's maneuvers or by using ultrasonic imaging, if necessary, to determine the baby's position in the uterus. Usually, with the fetus in vertex presentation (i.e., head down) this electrode is placed on the upper left or upper right quadrant of the pregnant maternal abdomen.

Figure 4:
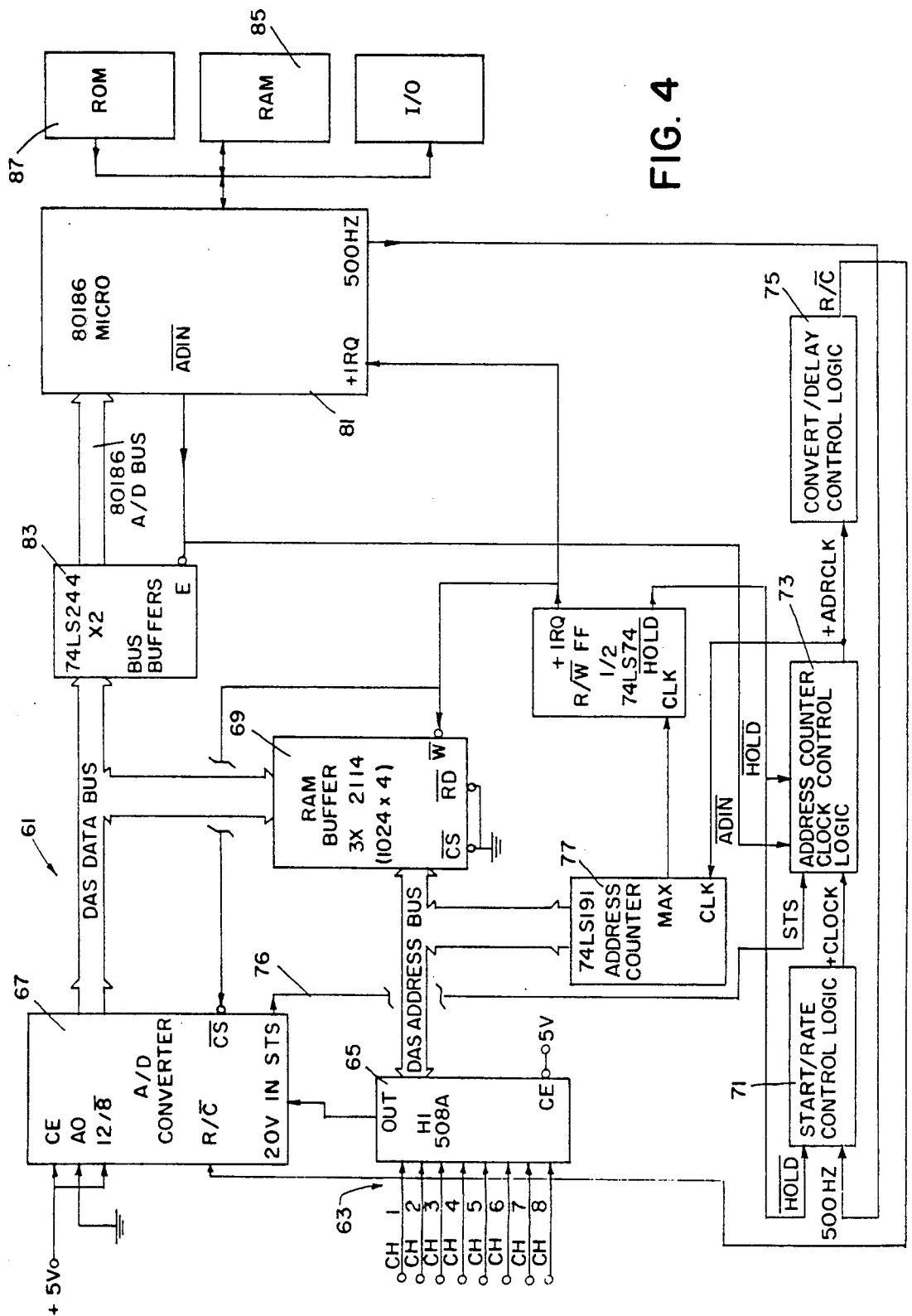
FIG. 4: Data Acquisition Circuitry Block Diagram.

The placement of the yellow and black electrodes 38 may be reversed. The preferred electrodes themselves are composed of Karaya Gel or Hydrogel material for ease of positioning, repositioning, and reuse. Also, they consistently provide high quality fetal ECG signals without the presence of 60 Hz power line interference when used with the analog front end signal processing circuitry 50 (FIGS. 4 and 5). It is important to note, that unlike previous fetal ECG abdominal mode FHR monitoring techniques without adaptive processing, the yellow and black abdominal electrodes are placed on the maternal abdomen at about the position of the fetal head and buttock to maximize the magnitude of the fetal ECG complex without regard for the magnitude of the interfering maternal ECG complex within the abdominal ECG signal as displayed on the CRT 9.

Following the placement of the abdominal electrodes, the number "1", displayed in the LED display 17 (FIG. 1), will disappear and the monitor will automatically display and update FHR, FHR beat-to-beat variability, and maternal heart rate on the seven segment display 17. If this does not automatically occur within approximately fifteen seconds the operator can improve the performance of the monitor by, first, viewing the fetal and maternal ECG on the CRT display 9, and then, by moving the position of the abdominal 38 or thoracic electrodes 39 (FIG. 2) improve the quality of the ECG data. By viewing the CRT display 9 the operator should see the presence of the larger maternal and smaller fetal ECG signal. By depressing the abdominal/fetal ECG button 11 the CRT should display only the fetal ECG signals following adaptive cancellation of the stronger maternal ECG signal. Then, as necessary, each of the abdominal electrodes 38 can be easily moved, in a circular fashion about its present abdominal location, for the purpose of obtaining a larger fetal ECG signal which can be observed on the CRT 11 and/or the chart recorder 19 using the FECG Mode switch 14 (FIG. 1). Then separately and independently of the abdominal ECG electrode locations 38, the thoracic electrodes 39 can be readjusted to provide improved maternal ECG cancellation as viewed on the CRT 11. In practice, it is usually only necessary to adjust the position of the red thoracic electrode 39 only slightly from side to side or up and down, since it is in common with the other thoracic electrodes 39 which provide thoracic signals one, two, three.

The description of the preferred embodiment is divided into two sections below: the Hardware Description and the Software Description.

A. Hardware Description

1. Analog Front End a. Functional Overview

The function of the analog front end circuit is low-noise, high-gain amplification of the maternal and fetal electrocardiogram (ECG) signals. Electrodes are placed in designated locations on the maternal abdomen and chest. Four leads or signals are collected from the pregnant subject; three leads or signals from the chest which contain only maternal ECG information, and one signal from the abdomen which contain both fetal and maternal ECG information.

b. Operational Description

Figure 3:
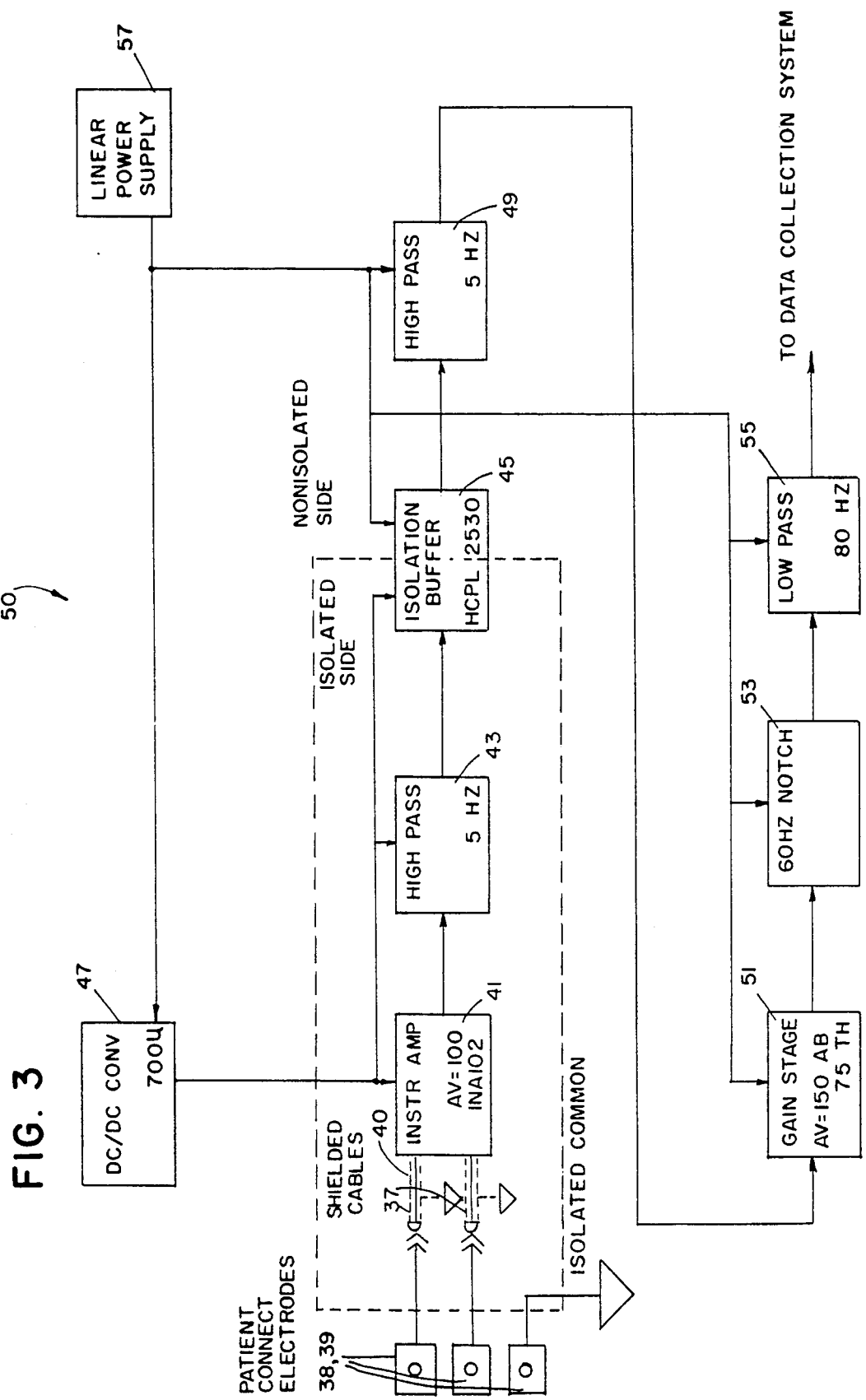
FIG. 3: Block Diagram of a Single Analog Front End Signal Processing Channel for Thoracic Channels (1-3) and Abdominal Channel (4).

Generally the signals are conditioned in the same manner as shown in FIGS. 3 and 4. Shielded cabling 37 is used to couple the signal from the electrodes 38 and 39 (FIG. 2) to the external connectors 3 and 5 (FIG. 1) of the FHR 186 Monitor. The internal cable 40 from the external connectors is also shielded. This is necessary to prevent radio frequency (RF) noise, generated by the microprocessors digital switching, from interfering with the low signal levels of the fetal QRS complex. The signal is applied to the inputs of a high AC input impedance instrumentation amplifier 41. Both the inputs to the instrumentation amplifier are shunted to ground with a pair of opposed diodes which clamp the voltage to 0.7 volts and 35K ohm series resistors are used to reduce leakage to the patient connections in the event of malfunction. The Burr Brown instrumentation amplifier INA102 was selected because it has an extremely high AC input impedance. The high input impedance allows the INA102 to compensate for the large source impedance imbalances generated by the skin/ECG electrode interface. The gain of this stage is internally selectable at amplifier 41 and is strapped to 100. Increased common mode rejection/noise performance could be realized by strapping the gain in excess of 100, e.g., to 1000 but this configuration with "karaya" gel or hydrogel ECG electrodes causes the output of amplifier 41 to saturate intermittently. The output is then fed into a 2-pole, high-pass Butterworth filter 43 with the cutoff at 5 Hz. This stage is needed to remove any DC offset and low frequency drift before the signal is applied to the input of the optical isolation buffer 45. The isolation buffer provides total patient electrical isolation. There is no common electrical reference between the input and output isolating the patient connections from the latter stages for safety reasons in the event of malfunction. The instrumentation amplifier 41, high-pass filter 43, and input to the isolation buffer 45 are consequently all powered by an isolated DC power source 47. The Burr Brown 700M DC/DC converter was chosen because it incorporates an internal shield on the input and output stages. An undesirable by-product of the optical isolation stage is the D offset and unstable baseline drift. A second, high-pass filter 49 identical to the first filter 43 follows the isolation buffer 45, effectively eliminating both problems. After this second high-pass stage, the signal is coupled into an op amp gain stage 51. The three thoracic channels which contain maternal information have a gain of 75 in this stage. The abdominal channel containing maternal and fetal ECG signals are amplified by 150 for total gains of 7500 and 15,000 respectively. After the gain stage, the signal is applied to a 60 Hz notch filter 53. This filter attenuates 60 Hz interference by 49 dB. The final output stage is a 3-pole Chebyshev low-pass filter 55 with a cut off set at 80 Hz. This filter attenuates higher frequency interference without removing energy from the fetal QRS complex. All operational amplifiers referred to in the above text are one of four in a quad op amp package LF444. The coupling between amplifiers within the quad package configuration is specified at $-120$ dB and is assumed to be negligible. A linear power supply 57 supplies power to elements 45-55.

2. Data Acquisition System a. Functional Overview

Figure 6:
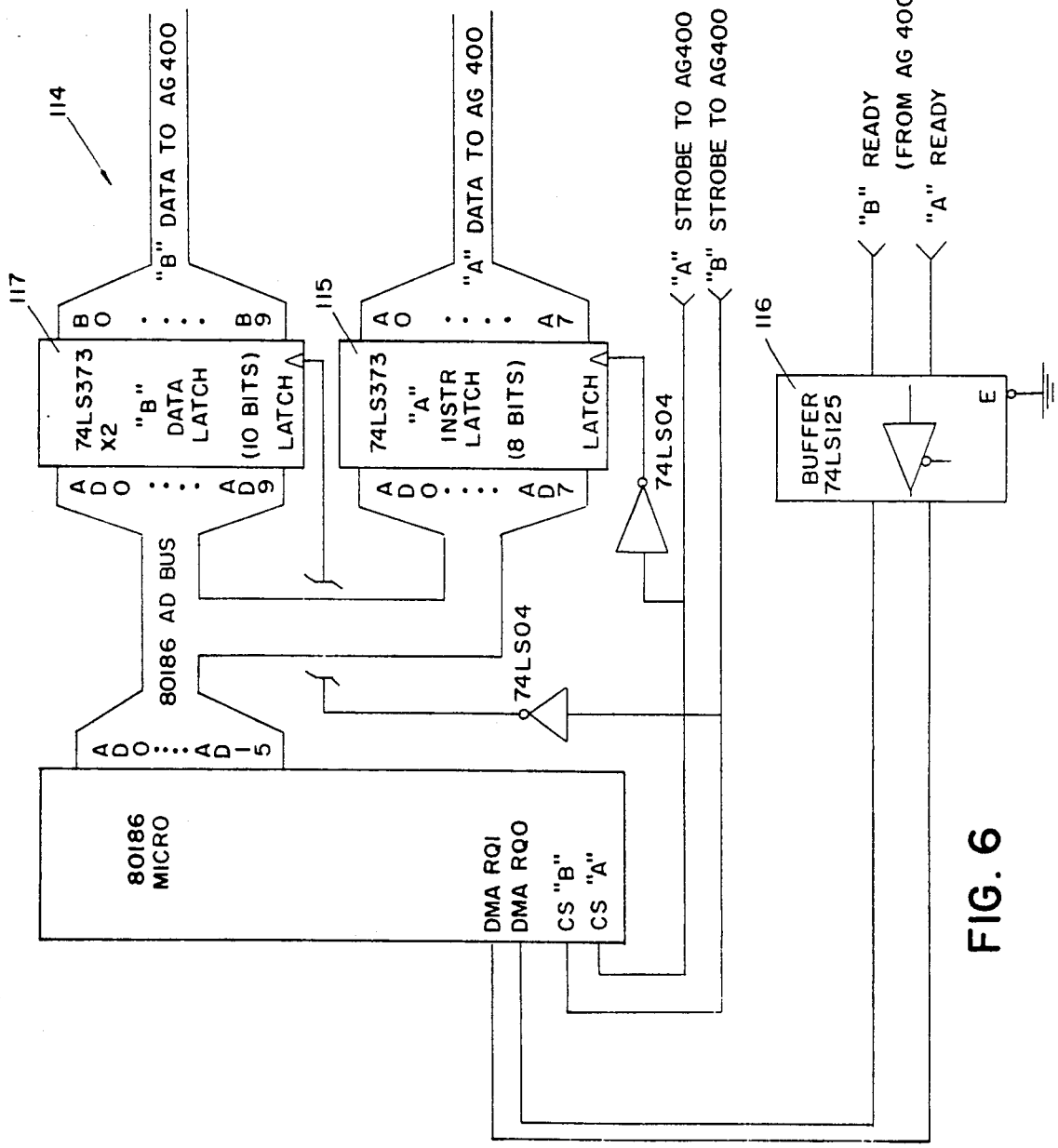
FIG. 6: AG-400 Chart Recorder Interface Circuitry Block Diagram.

The data acquisition system 61 shown in FIGS. 5 and 6 on the microprocessor PC board takes its inputs from the analog front-end PC board. The four conditioned signals 63 are applied to the input of a Harris HI-508 multiplexer 65. Channels 1, 2, and 3 represent data collected from the maternal thoracic region and contain only maternal electrocardiogram (ECG) information. Channel 4 represents data collected from the maternal abdominal region and contains both fetal and maternal ECG information. The output of the analog multiplexer is fed into the analog input pin of the HI-674 analog-to-digital (A/D) converter 67. Digital sampling of these signals is accomplished in groups of eight channels and is synchronized to a 500 Hz sample rate clock. The digital signal processing (DSP) algorithms used for processing the data assume the data is collected at corresponding points in time from each channel of the data that is collected simultaneously in time, therefore, the samples are buffered until all channels are A/D converted. The data acquisition system then requests an interrupt from the processor which gathers the group of buffered data and begins processing.

b. Operational Description

The special function of the data acquisition system as implemented is that it allows the data collection function of the process to occur with very little microprocessor intervention, while absolutely minimizing the delay between the sampling of each channel. The following signals are assumed present at the positive edge of the sample rate clock: $\overline{HOLD}$ = not true = HIGH—This condition will allow the positive edge of the sample rate clock to be gated through to the convert/delay control logic.

A0 = A1 = A2 = 0 = LOW—When this condition is true, the channel corresponding to input #1 is applied to the analog input of the HI674 A/D converter 67, and the RAM buffer address is pointing to location #0 in the 8×12 bit RAM buffer 69 (Queue).

$R/\overline{W}$ = WRITE = LOW—This condition will allow converted sample data from the A/D converter 67 to be written into the RAM buffer 69 in the locations corresponding to the address specified by A0, A1, A2.

The +INT = 0 = LOW—When driven high, INT will trigger the only interrupt necessary to service the data acquisition system as implemented. The advantage realizes here is that, a minimum of software is needed to drive the data collection system, therefore saving microprocessor time for processing data.

With all the previous conditions met, and realizing the microprocessor is free to perform other tasks throughout the entire conversion process, the data collection sequence begins with the positive edge of the sample rate clock 70. The start/rate control logic 71 is transparent at this point, as is the address counter clock control logic 73, so that the rising edge of the sample rate clock is gated through to the convert/delay control logic 75. Three microseconds later, $R/\overline{C}$ is driven low for approximately 1.5 microseconds to initiate a conversion. Approximately 150 nanoseconds later, the STS line 76 from the A/D converter is driven high, to indicate a conversion is in progress. This state change of STS has no effect on RAM buffer address or the analog multiplexer address, as the address counter 77 has a positive edge triggered clock and STS is inverted before being applied to the address counter's clock in the address counter clock control logic 73. Approximately 12 microseconds later, (for the HI674 A/D Converter) STS will be driven low, indicating conversion complete. STS is inverted and gated in the address counter clock control logic to cause the data to be written into location #1 in the RAM buffer 69. The analog multiplexer 65 is now pointing to Channel 2 and applying it to the analog input of the 674 A/D converter, while the valid data from Channel 1 is stored in RAM buffer Location #1. Additionally, STS is also gated through to the convert/delay control logic 75 where it gets a 3 microseconds delay before driving R/C low again for 1.5 microseconds and causing another sample, Channel 2, to be converted by the A/D converter for storage. This continues until Channel 8 is addressed and converted, driving STS low. This action indicates conversion is complete and Channel 8 is stored as the address counter is reset to 000. $\overline{HOLD}$ driving low prevents STS from gating subsequent conversions and also inhibits future sampling until the interrupt service routine clears this hold condition. This prevents corrupted data by eliminating the possibility of missing a sampling interval. Finally the +INT line is driven high by the $R/\overline{W}$ Flip Flop 79, and the microprocessor 81 immediately enters the interrupt service routine. This routine responds by simply doing 8 inputs at the specified A/D address. The samples are addressed and applied to the data bus buffers 83 for collection by the microprocessor. The rising edge of the I/O chip select (ADIN) from the 80186 microprocessor is used to clock the counter address by gating through address counter clock control logic 73 and clocks the RAM buffer address to the next data point for input. The analog multiplexer can be disabled at this point, but its outputs are irrelevant because the HI674 A/D is disabled by the +INT line applied to its $\overline{CS}$ line. The automatic clocking of the counter address by ADIN makes it possible for a single interrupt service routine to input all 8 samples through a single I/O port. After inputting the last buffered data point in the queue, the hold condition is reset. This is critical in order to gate the next rising edge of the sample rate clock through the start/rate control logic, then to the convert/delay control logic, eventually causing 8 more data points to be converted. This approach requires less software to drive it and less microprocessor time to service and collect data, while minimizing delays between samples, thereby making it the best choice for this process.

3. Microprocessor a. Functional Overview

The function of the microprocessor 81, as implemented in the FHR 186 monitor, is to provide all the computational power for the electrocardiographic digital signal processing (DSP) algorithms used. The processor is also responsible for maintenance of the data acquisition system and detecting user input via the switches and push buttons. Outputs for peripherals receive instructions and data via the microprocessor bus.

b. Operational Description

The microprocessor employed is the Intel 80186 which operates at a maximum clock frequency of 10 MHz. All that is required to generate this is an external crystal of twice the desired operating frequency (i.e. 20 MHz). The package contains an oscillator capable of generating the 10 MHz internally. The 80186 also integrates many useful peripherals, allowing a lower total chip count and simplifying PC board and design. Included in the 80186 package are an interrupt controller, three channel timer, bus controller and DMA controller that make the 80186 ideal for this small dedicated system. The microprocessor system incorporates a bank of static random access memory 85 (RAM) capable of storing 64K bytes of information. The system also contains a 16K bank of ultra violet electrically programmable read only memory 87 (UV-EPROM) which contains the program that operates the system. Other miscellaneous TTL logic is included in the design for various logical and gating operations. The operation of the processor can be considered to begin by resetting the system via power-up reset, or if the unit cover is removed, by using the more direct hardware push button which is available for the service technician. Upon reset, the address of the first fetch is forced to a reset address FFFF:0 (HEX) this area is 16 bytes below the top of memory and will cause the UV-EPROM to be selected. The instruction located in this location is a jump to the beginning of the actual program code. Execution of the monitor program begins upon the completion of this jump instruction. (See B. Software Description)

4. Input/Output Devices (Operator Interface)

a. CRT Display

1. Functional Overview

The cathode ray tube (CRT) display, as implemented in the FHR 186 monitor, uses an electrostatic CRT tube to display an analog representation of digital data. It provides a means for the operator to view raw data from any one of the ECG inputs (test mode), or operationally, data from the abdominal ECG input after cancellation of the maternal complex (i.e. fetal complexes only). The sweep rate is approximately once every 3.5 seconds or, if desired, the operator can "freeze" the display indefinitely with Freeze/Scan push button provided. The function of the CR and driving circuitry in the entire fetal ECG monitoring process is unique in that it is the operator's best indicator as to whether the thoracic ECG leads are in the optimum position to provide maternal ECG cancellation for a given patient. The CRT can also be helpful in determining whether the abdominal ECG leads are properly positioned to maximize the fetal ECG signal, irrespective of maternal ECG amplitude as in prior monitoring schemes. The operator can put the CRT in the mode to display abdominal data results after cancellation and position the leads and immediately receive feedback.

2. Operational Overview

Figure 7:
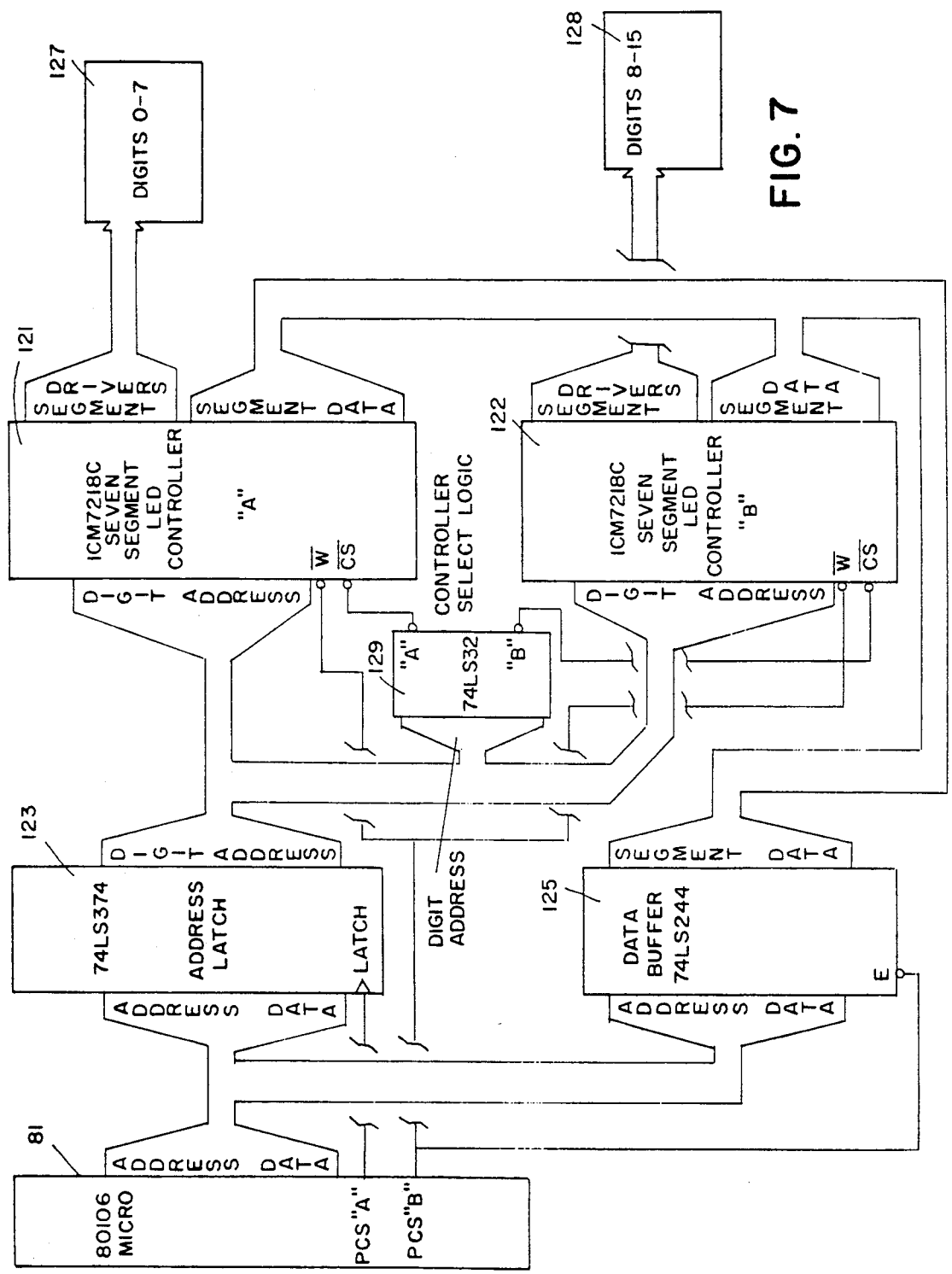
FIG. 7: Block Diagram of Seven-Segment LED Circuitry.

The display buffer circuitry, shown in FIGS. 7 and 8, is the source of the data that is ultimately displayed on the CRT screen. Basically, the circuit 90 has a portion of random access memory 91 (screen buffer) that is addressed by two different sets of address counters 93, 95 through a set of multiplexers 97 (video multiplexer). The multiplexers control which set of counters (data address counter 93 or refresh address counter 95) will establish the address of the screen buffer, while other logic will determine whether the screen buffer is being read from or written into. The master clock 99 for the CRT circuitry is the 10 MHz oscillator from the 80186 divided by 64 (6.4 microsecond period). This signal is used to clock the refresh address counters. Since there are 2048 locations in the screen buffer, it follows that one refresh of the screen requires 13 milliseconds (i.e., 6.4 microseconds * 2048). A trigger pulse is generated as the refresh address counters reach position 0, which indicates the system is at the beginning of the screen buffer. This trigger pulse will be used to synchronize the horizontal ram generator to the beginning of the video data in the screen buffer. The period of the horizontal ramp is determined by the refresh time of 13 milliseconds, therefore, the frequency of the horizontal ramp is approximately 76 Hz (i.e., 1/13 milliseconds). The display circuitry can be assumed to be in either one of two modes: CRT refresh, or refresh disabled while the screen buffer is updated. Update of the screen buffer is accomplished by writing video data to the CRT data latches 181 every 2 milliseconds. Asynchronously from that event, the refresh address counters are disabled momentarily every 1.6 milliseconds. The write enable to the screen buffer is strobed while the CRT data latches 181 are enabled to transfer the video data from the CRT data latches to the screen buffer for subsequent refresh and display. This timing is hardware controlled and is equal to the refresh rate of 6.4 microseconds times 256. The design of the controller is such that if it is not updating the screen buffer, it is refreshing the CRT. Refresh is accomplished by toggling through the screen buffer addresses while the screen buffer is in read mode and clocking the CRT digital-to-analog (D/A) data buffers 103. The data in the screen buffer is clocked through the CRT D/A data buffers and applied to the D/A converter 105. The analog signal out from the D/A converter is then applied to a low-pass filter 107 to remove the digitization steps and D/A switching noise before being coupled to the vertical deflection amplifier 109. The synchronized horizontal ramp generator 111 output is applied to the horizontal deflection amplifier 113, then the amplified vertical and horizontal signals are applied to the vertical and horizontal deflection plates of the CRT tube.

b. AG400 Chart Recorder

1. Functional Overview

The AG400 chart recorder is the only way to get hard copy of the monitor's outputs. This unit is capable of displaying one to four channels of digital data simultaneously. In addition, it is able to micro-step the paper to achieve all the standard chart recorder speeds commonly in use and adapt to new standards.

2. Operational Description

Figure 9:
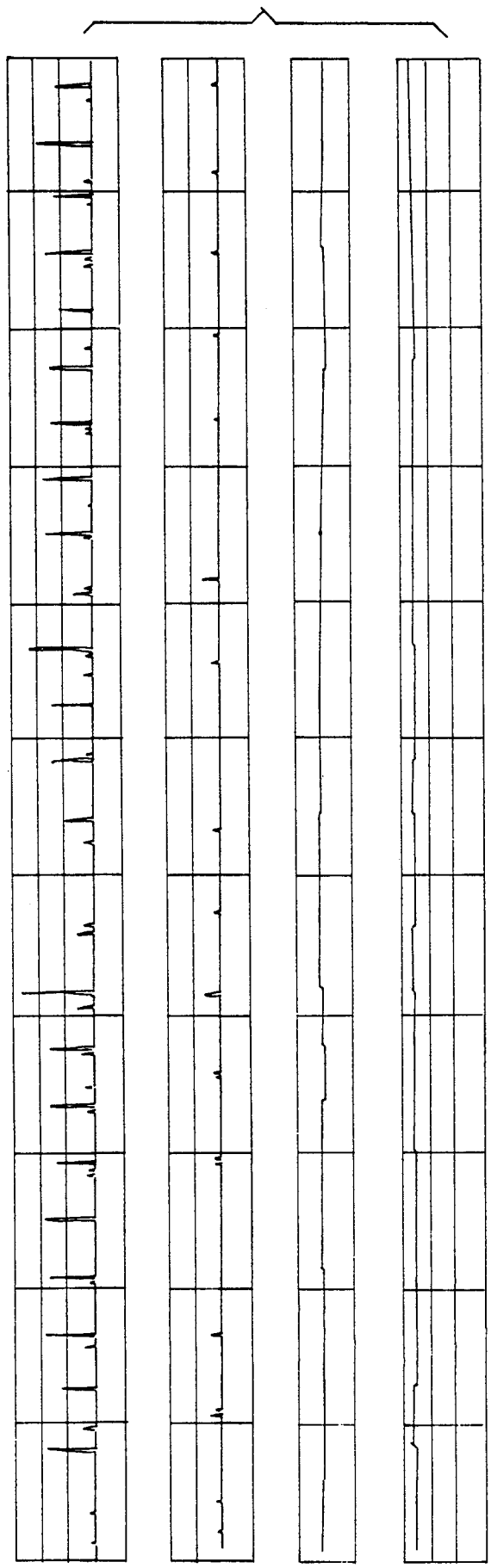
FIG. 9: Voltage-time graphs (@25 mm/sec) illustrating various stages of the fetal ECG detection, fetal heart rate, and fetal heart rate variability computation (FBPM) module: a) (upper tracing) following the matched filter stage, the fetal ECG data is squared providing improved fetal signal level to background noise level for subsequent detection; b) (second tracing) following the squaring of the fetal signal-and-noise, the noise level alone is plotted here; c) (third tracing) the fetal ECG detection level is plotted here from the fetal ECG signal level (a) and background noise level (b); d) and the instantaneous fetal heart rate tracing obtained from the application of the detection threshold (c) to the signal (a) is plotted here with a rate scale compressed into 2.0 cm to plot the full range of 30 to 210 bpm and the time scale expanded to one second per 25 mm.

The AG400 is purchased as a unit and replaced as a unit. Therefore, the details of its operation will not be discussed. The one section that needs to be examined is the AG400 interface 114 in FIG. 9 to the 80186. Data is output to the AG400 through the data port at 210H and the instruction port at 290H. The instructions or data from the processor are latched into 74LS373 (instruction latch 115 or data latch 117) on the rising edge, of the AG400 I/O chip select. The falling edge is used to latch the data into the AG400. The AG400 will then assert a "busy" signal. The AG400 will not accept instructions or data until the busy signal is withdrawn. In order to service the AG400 without tying up the processor with polling, the direct memory access (DMA) request lines are employed to monitor the status of the busy lines through transparent buffer 116, thus allowing AG400 maintenance to run independently of the 80186 processing.

c. Seven-Segment LED Display

1. Functional Overview

The light emitting diodes (LEDs) provide the operator with vital information about the patients (maternal and fetal). Four outputs are available constantly in large, easy-to-read, ½ inch digits which include:
1. Fetal Heart Rate
2. Fetal Heart Rate Variability
3. Maternal Heart Rate
4. Uterine Activity

2. Operational Description

Figure 10:
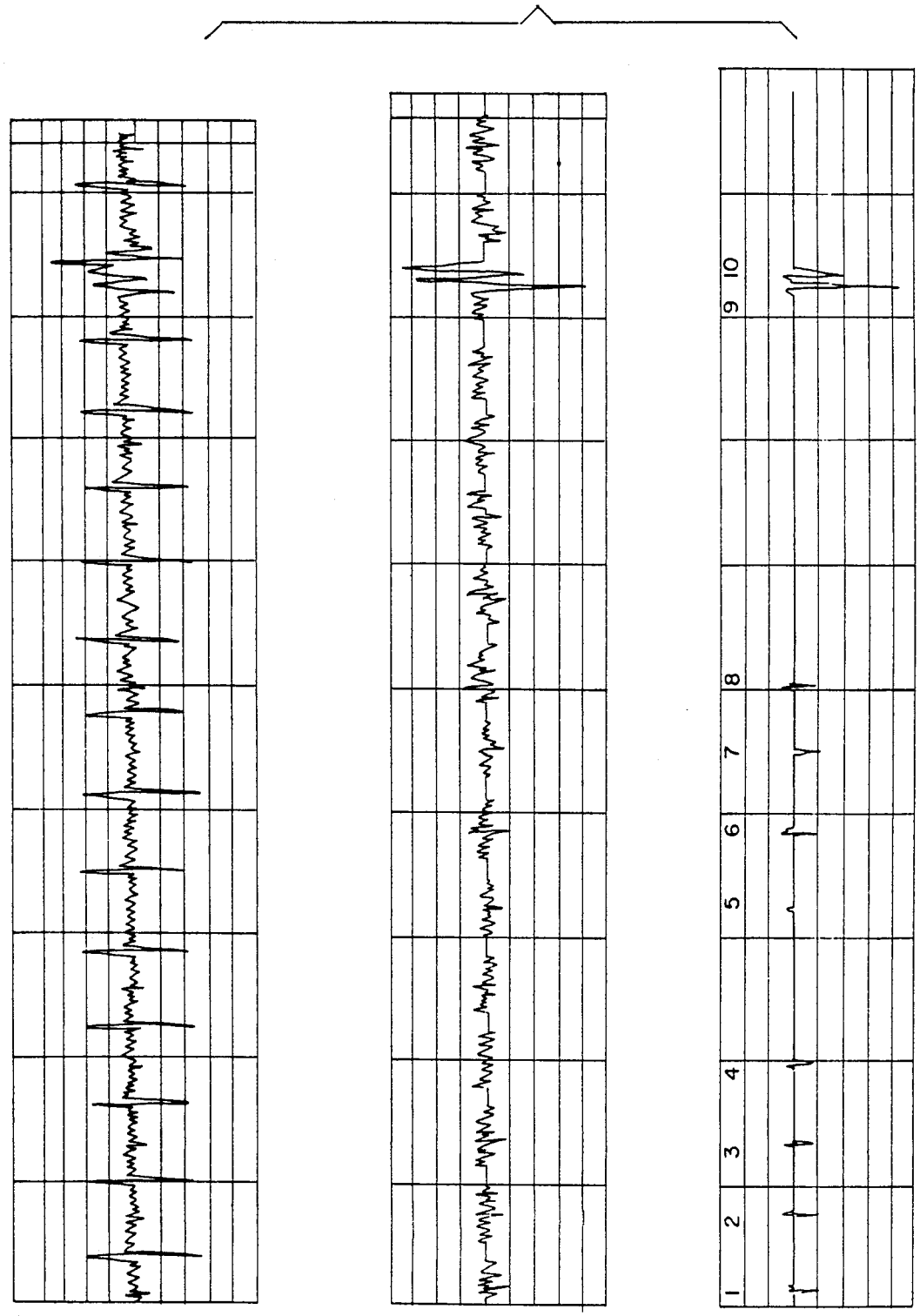
FIG. 10: Voltage-time graphs (@25 mm/sec) illustrating various stages of the Matched Filter Start Up (MFSU) Subroutine:
 a) (upper tracing) a portion of the data collected at the output of the analog front end of Channel 4 displayed maternal ECG and fetal ECG complexes; b) (second tracing) the upper tracing signal with maternal ECG complexes excised;
 c) (lower tracing) the fetal ECG complexes (fetal windows) selected by the MFSU Subroutine from the excised signal.

The control of the LEDs is accomplished as shown in FIG. 10 with the help of two seven-segment LED controllers 121, 122 (Intersil ICM7218C). A write sequence consists of two steps. First, the desired digit is addressed by outputting a digit address to a 74LS374 (Address Latch 123) at location 86. Second, the data for that digit is sent to a 74LS244 (Data Buffer 125) at location 89. Digit positions 127, 128 are 0-15 and are randomly addressable as additional logic 129 determines which controller to access. Refresh is accomplished automatically by the controllers.

d. Speaker and Beat LED

The speaker is provided for audio feedback that the monitor is in continuous operation. The beat LED is provided for visual feedback of continuous monitoring operation (this output is synchronous with the speaker tone).

e. Push Buttons

All the push buttons and rotary switches are read by the microprocessor at I/O locations 8C to 8E. Each of the three eight-bit buffers are polled periodically for switch closures. Upon detecting a switch closure, the program will effect the appropriate response. A description of each button and its function is summarized below.

| Button | Function |
| --- | --- |
| Record | Activates AG400 to record processed data in selected mode. |
| Fetal/Abdominal | Toggles CRT Display between the display of raw data or the display of the results of cancellation. |
| Freeze/Scan | Toggles CRT to continuously display and update abdominal data or to display the last 3.5 seconds of data in FREEZE mode. |
| Start | Causes monitor to execute a start-up procedure. |
| Test | When activated, allows individual CRT display of each abdominal and thoracic ECG channel by sequentially depressing the Fetal/Abdominal CRT button. | f. Rotary Switch

The rotary switch selects the mode for the AG400 output. A description of the switch settings and their functions follows:

| Switch Setting | Function |
| --- | --- |
| FECG | Provides abdominal ECG data and cancellation results (fetal ECG only) at 25 mm/sec. |
| FILTER 1 | Provides canceled fetal ECG data and matched filter output at 25 mm/sec. |
| FILTER 2 | Provides squared data output, squared noise output, threshold level output, and instantaneous fetal heart rate at 25 mm/sec. |
| FHR | Provides FHR, FHR variability, and uterine activity at 3 cm/min. |

B. Software Description

1. Real-Time Operating System

The fetal monitor must function in a real-time setting. Thus the system software must input data continuously that has undergone analog to digital (A/D) conversion, process this data and generate various forms of continuous output. While this is going on, the operating system allows the operator to change the system parameters and functions with push button and switch settings that the system monitors. See FIG. 11 for an overview flow chart of the monitor software.

---

FLOWCHART - I
OVERVIEW OF FETAL MONITOR SOFTWARE

| START |

---

Because of the systems real-time requirements, the data collection, switch inputs, and outputs are controlled by hardware interrupts at regular, timed intervals. A sample rate clock is generated by one of the processor's timers every 2.0 msec. The sample rate clock causes the data acquisition hardware to collect eight channels of data. Once the eight channels are collected an interrupt is sent to the processor which executes an interrupt service routine, SAMPLE_INT 155, which causes the data samples to be input from the data acquisition hardware to the microprocessor.

This interrupt service routine, SAMPLE_INT, collects eight channels of 12 bit A/D data, but presently stores only channels 1, 2, 3 and 4 in an input buffer. (The remaining channels will be used later.) The routine then outputs waveform data to a CRT display, fetal heart rate to a seven segment LED display, and sends waveform and/or fetal heart rate and variability data to a thermal chart recorder through one of the processor's DMA channels. SAMPLE_INT calls the DMA interrupt service routine, DMA_INT 156, which sets up a DMA controller to send one channel of data, asyncronously, to the chart recorder. DMA_INT sets up an interrupt generated by the DMA controller each time it is exited, causing DMA_INT to be executed again when the chart recorder is not busy, DMA_INT repeating in this way until all chart recorder channels have been sent. This output data is accessed from an output buffer in order to allow processing to operate asynchronously from the interrupt service routine described above.

Every 100 msec another interrupt is generated by a second timer integrated in the processor chip. This interrupt causes the execution of an interrupt service routine, KEY_INT 157, that reads and debounces the front panel push buttons of the monitor, and then executes the functions of the buttons that are depressed.

The three interrupt service routines described above are enabled only after the execution of the software module, INIT 151, that initializes the system. This module initializes the front panel lights and displays, the chart recorder and DMA channels, interrupt vectors for the service routines described above, and executes a quick system test. Once the interrupts are enabled 153, the service routines are executed immediately after their respective interrupt strobes occur. When not servicing the interrupts, the processor is executing the main routine 159, which contains all the signal processing routines. This main routine repeats every 500ms 161. The main routine starts by moving data from the interlaced input buffer into single channel arrays 163. These single channel arrays containing raw data are processed, generating intermediate and final result arrays all of which correspond to the 500 msec window of time in which the raw data was sampled. The last section of the main routine, STORE_ARRAYS 179, places the data from the output arrays into the interlaced output buffer from which the input/output service routine can asynchronously output the data. Because of the present methods of buffering and array processing, the time delay between signal input and the results output on the chart recorder is 3.0 seconds. In the future, this delay can be reduced to less than one second. The main software routine must repeat every 500 msec, but actually finishes in a much shorter period. Execution of the main loop is controlled by a conditional test of the input buffer pointers, to make sure 500 msec of data (250 sets of data points) are collected before the next main software routine is executed 161.

2. Digital Signal Processing

All signal processing occurs in the main routine of the system software as described above. Since the object of the fetal heart monitor is to provide a reliable fetal heart rate and fetal heart rate variability, the final result of the software signal processing routines must be the rate and variability of the fetal signal. In order to obtain these results, four channels of data are presently used for processing. The first three are thoracic signals from the pregnant mother. These are used to generate an orthogonal vector set of the mother's ECG. The fourth signal is recorded from the mother's abdomen and contains both the maternal and fetal ECGs. The orthogonal set is used to remove the maternal ECG from the abdominal signal leaving the fetal ECG complexes and some residual noise. The algorithm used to remove the maternal signal is referred to as the cancellation algorithm, CANCEL 167.

Further processing is skipped over until the matched filter startup routine, MFSU 171 is successfully executed. The MFSU subroutine is executed automatically after three seconds of data are collected or manually by pressing the restart push button. MFSU uses ten potential fetal peaks detected in approximately four three-second data segments (i.e., 12 secs) of the abdominal data channel (A1) to find a suitable 60 msec (i.e., 30 point) fetal window to be used to match filter the fetal signal. It also calculates an initial threshold for fetal peak detection based on an initial calculation of the fetal peak level and noise peak level in the data.

Once the startup routine is executed, the fetal signal-to-noise ratio is increased by the use of a matched filter subroutine, MFLTR 171, using a 30 point filter window. The matched filter is applied to the result array of the CANCEL routine. The signal-to-noise ratio of the matched filter result is improved further by squaring the positive values of the matched filter output. This is done by the SQUARE subroutine 173, producing a 500ms (250-point) array which is peak detected by the next processing routine, Fetal Beats Per Minute, FBPM 175.

In the FBPM (Fetal Beats Per Minute) routine, intervals between peak detections are measured and converted into fetal heart rate and fetal heart rate variability and the results are placed into arrays that are time aligned with the other output arrays. Fetal heart rate and variability generated by the FBPM routine are displayed on both the chart recorder and the seven segment displays. The Maternal Beats Per Minute routine, MBPM 165, is also included to determine the maternal heart rate from the channel 2 thoracic data array, T2. The maternal heart rate determined from this routine is displayed only on the seven segment display. See FIG. 14 for graphs of wave-form data showing raw A1 data 25, canceled A1 data 23, and match filtered output data 27. See FIG. 9 for graphs of square data 22, noise data 24, threshold levels 26 and rate results 28. See FIG. 18 for a display of the standard rate 33 and variability 35 output.

a. CANCEL (Cancellation Routine 167, FLOWCHART - I)

T1, T2 and T3 are element arrays of raw thoracic ECG data. The arrays each contain 250 continuous digital samples collected at 2 msec intervals, i.e., 500 msec. A1 is an array of equal length of raw abdominal ECG data. The average value of each raw data array is computed and assumed to be the DC offset of that array. This offset is subtracted from each element of the four input arrays to produce arrays with their offsets removed for further processing.

The following calculations are used to find an orthogonal set (PHI1, PHI2 and PHI3) for each continuous 500 msec data segments without regard for the presence, partial presence, or absence of the maternal QRS ECG complex which is to be canceled.

1) Calculate PHI1(J) from the data T1(J):

$$PHI1[J] = T1[J] \text{ for } J = 1 \text{ to } 250$$

2) Calculate PHI(2) from the data T2(J) and PHI1(J):

$$SUMN21 = \Sigma(T2[J] * PHI1[J]) \text{ for } J = 1 \text{ to } 250$$

$$SUMD01 = \Sigma(PHI1[J] * PHI1[J]) \text{ for } J = 1 \text{ to } 250$$

$$A21 = SUMN21/SUMD01$$

$$PHI2[J] = T2[J] - A21 * PHI1[J] \text{ for } J = 1 \text{ to } 250$$

3) Calculate PHI(3) from data T3(J) and PHI1(J) and PHI2(J):

$$SUMN31 = \Sigma(T3[J] * PHI1[J]) \text{ for } J = 1 \text{ to } 250$$

$$SUMN32 = \Sigma(T3[J] * PHI2[J]) \text{ for } J = 1 \text{ to } 250$$

$$SUMD02 = \Sigma(PHI2[J] * PHI2[J]) \text{ for } J = 1 \text{ to } 250$$

$$A31 = SUMN31/SUMD02$$

$$A32 = SUMN32/SUMD02$$

$$PHI3[J] = T3 - A31 * PHI1[J] - A32 * PHI2[J] \text{ for } J = 1 \text{ to } 250$$

Once the PHIs are calculated, these are used to calculate a set of coefficients (B11, B12, B13) that describe the relative weight of the three orthogonal vectors in each abdominal signal. The coefficients are then used to remove the maternal QRS from the abdominal signal.

4) Calculate the B coefficients from the abdominal data A1(J) and A2(J) and the PHI's:

$$SUMA11 = \Sigma(A1[J] * PHI1[J]) \text{ for } J = 1 \text{ to } 250$$

$$SUMA12 = \Sigma(A1[J] * PHI2[J]) \text{ for } J = 1 \text{ to } 250$$

$$SUMA13 = \Sigma(A1[J] * PHI3[J]) \text{ for } J = 1 \text{ to } 250$$

$$SUMD03 = \Sigma(PHI3[J] * PHI3[J]) \text{ for } J = 1 \text{ to } 250$$

$$B11 = SUMA11/SUMD03$$

$$B12 = SUMA12/SUMD03$$

$$B13 = SUMA13/SUMD03$$

5) Apply the B coefficients to the PHI's to cancel the maternal ECG projection from the abdominal ECG data:

R2NEW[J]=A2[J]−B21 * PHI1[J]−B22 * PHI2[J]−B23 * PHI3[J] for J=1 to 250

RNEW is the result array containing the fetal signal with the maternal signal removed.

6) Integer Value Calculations:

The calculations shown above are implemented in the microprocessor using integer values rather than floating point calculations. Arrays T1, T2, T3, A1, PHI1, PHI2, PHI3, and RNEW are composed of single precision integer value elements. Results of multiply-accumulate functions, SUMN21, SUMN31, SUMN32, SUMA11, SUMA12, SUMA13, SUMA21, SUMA22, SUMA23, SUMD01, SUMD02 and SUMD03, are double precision integers. Coefficients, A21, A31, A32, B11, B12 and B13 are represented by two words that can be described by the following equation:

VALUE=WORD1 * $2^{(-WORD2)}$

This method of representation allows all of the above calculations to be done in real time, avoiding time consuming floating-point calculations. The division routine used to calculate the coefficients uses double precision integers as the input numerator and denominator. These values are left justified and WORD2 of the result is determined from the difference in shift count for the justification of the numerator and denominator. Using a modified subtract-replace division algorithm, the quotient of the left justified numerator and denominator is calculated and stored as WORD1.

b. MFSU (Matched Filter Startup Routine)

The purpose of the MFSU routine is (1) to find a 30-point fetal ECG template window to be used for the matched filter algorithm, and (2) to calculate an initial threshold level for peak detection of the SQUARE output, based on an estimated peak signal level and an initial estimate of the noise level in the SQUARE output. See FIG. 12 for a flowchart of the MFSU subroutine.

---
FLOWCHART - II

MFSU
---

The 30-points for the fetal ECG template window are extracted and stored by first collecting groups of three seconds of raw data from channel 2 (T1) and channel 4 (A1). This data is placed in arrays T2_LONG and A1_LONG 181. Maternal complexes are then excised from A1_LONG 183 by peak detecting in T2_LONG using a threshold that is 50% of the maximum data amplitude in T2_LONG and removing 200ms of corresponding data points in A1_LONG, centered around each detected maternal complex. The excised A1_LONG data now includes only fetal complexes and noise, although some, all, or portions of some fetal complexes in the three second start-up window may also be excised.

This excised data is next peak detected for fetal complexes 185 using a threshold that is 75% of the maximum excursion of the excised data in A1_LONG and 60 msec centered windows are then stored for each potential fetal complex detected. (Some potential fetal complexes may be noise peaks.) The remaining MFSU procedure requires 10 potential fetal templates (windows), each having a time period of 60 msec. (At 2 ms/sample, each template consists of 30 samples, and the storage of 10 templates requires a 30×10 array.) The 30 sample points are chosen to be centered about each potential fetal peak maximum. The maternal excision and fetal peak detection and storage process is executed every three seconds until at least ten potential fetal peaks are stored in a 30×10 fetal template array 187. A 10×10 array of normalized correlation coefficients of every potential fetal template in the fetal template array with every other fetal template in the array and itself is then calculated 189.

Next, the two largest normalized cross correlation coefficients for each fetal template in the array are averaged 191. The fetal peak with the largest average cross-correlation coefficient is selected as the matched filter fetal window if its average cross-correlation coefficient is greater than 0.75 193. The selection of a fetal window terminates in the storage of the 30 coefficients (data points) in the matched filter fetal window array, FW 195. If the average correlation of this peak is not greater than 0.75, then the FW is thrown out 197, and the MFSU is exited until 3 more seconds of data are collected 199, allowing the MFSU to attempt to find a FW once again.

Once the FW coefficients are stored, the initial threshold for fetal peak detection, FBPM_THRSH, is calculated as 75% of the square of the autocorrelation of FW 201. This will be used for peak detection within the SQUARE routine output array. The initial value of the noise level is computed from the last 500 msec of data which is taken from the A1_LONG array, then matched with the FW array using MFLTR and squared using SQUARE 203. Fetal peaks in this squared data are detected using the FBPM_THRSH, and excised using a 60 msec window 205, centered about the fetal QRS complex. The maximum value in the remaining data is stored as the initial NOISE value 207.

c. MFLTR (Matched Filter Routine 171, FLOWCHART - I)

The output array of CANCEL, RNEW, contains fetal ECG signals, but these are relatively small, thus a matched filter is applied to increase the signal-to-noise ratio of the fetal signal to the background noise level. The filter window used in the matched filter consists of 30 integer values (coefficients). To provide continuous output, while still maintaining the 500ms cancellation window duration structure of the main routine. The division by 256 is simply a scaling function.

RMFNEW[J](FW[J] * R[J])/256 for J=1 to 250 d. SQUARE (Squaring Routine 173, FLOWCHART - I)

This procedure takes all positive values in RMFNEW and squares them, placing the results in array SQR. All negative values in RMFNEW are set to zero in the output array, SQR. This square function produces a non-linear improvement in signal to noise level.

e. FBPM (Fetal Beats Per Minute Routine 175, FLOWCHART - I)

FBPM (Fetal Beats per Minute) uses the SQR array data to peak detect the fetal signals. Then, by measuring the time interval between adjacent fetal peaks, i.e., the number of points between each detection, the instantaneous rate for each beat-to-beat interval is computed in beats per minute. Fetal heart rate variability is calculated on a beat-to-beat basis by finding the positive absolute value of the difference in rate between the present rate and the previous rate, and reporting it in beats per minute. Each peak detection has a maximum error of one-half the sampling time period. Therefore, the maximum fetal electrocardiogram R-R interval error is 2.0 msec, or 0.7% maximum worst case error at 210 bpm. See FIG. 13 for a flowchart of the FBPM subroutine.

---

FLOWCHART - III
FETAL BEATS PER MINUTE
SUBROUTINE FLOWCHART

FBPM

---

Three output arrays are generated by the FBPM routine. The first two output arrays, BPM and VAR, contain data that will be sent to the chart recorder. BPM contains the rate data and VAR holds the variability data. The third array, SEV_SEG, is used for data that will be sent to the seven segment display. This array holds both rate and variability data. The data in these arrays are all time aligned with the SQR array data.

Fetal peaks in the SQR array are detected by the FBPM routine when the magnitude of an array value, with the same sign as the threshold, exceeds the threshold magnitude, SQR_THRSH 209. Once a peak is detected, the routine finds the position of the peak maximum by reading subsequent values until the sign of the slope of the peak reverses 211. Next, the position of the peak value in the SQR array is stored, and the previously calculated rate and variability are stored in the output arrays, from the points in each array corresponding to the last detection, or from the beginning of the array if the last detection was in a previous array, to the points corresponding to the present detection 213. When the detection process reaches the end of the SQR array 208, the last rate and variability values are used to fill the output arrays from the last corresponding detection points 215. In this way, the rate and variability values are stored in the output arrays for the period of time corresponding to the detection point used to calculate them.

Each time a detection is made the new rate is calculated by determining the number of array points since the last detection 215. Since the data points are collected every 2.0 msecs, the period in seconds for this interval is two times the number of points between detections. Conversion of the interval to a rate is a straight formula calculation 217.

The fetal ECG square threshold detection level, SQR_THRSH, is modified with each new detection based on an array of eight fetal ECG peak values and the last estimate of the noise level. The FBPM routine starts by filling this array with the amplitudes of the first eight detected peaks, using the initial threshold (i.e., 75%). With each new detection, that peak level is stored in an array of eight peak values, and the oldest value is thrown out of the array 221, if the interval since the last peak detection is greater than 286 ms 219. Each new threshold is set halfway between the average of the fetal peak array and the last noise estimate 223. If the interval since the last fetal peak detection is less than or equal to 286 ms, the peak value of the detected fetal peak is thrown out and the threshold isn't updated 220.

A separate array of eight fetal rate values is set up and maintained by the FBPM routine. The FBPM routine starts by filling this array with the first 8 fetal rate measurements. Once the array is filled, each new rate is stored in the fetal rate array, and the oldest value in this array is thrown out 225. Each time the rate array is updated, the rate running average is calculated in the following way 227. First, a temporary average is calculated for the 8 rate values presently in the array.

Next, each rate value in the array is compared with this temporary rate average, and if the difference between the two rates is less than 30 bpm, then this rate value is used in the calculation of the rate running average. As a result, the rate running average is calculated from reasonable rate values only. As described in the next paragraph, the FHR rate running average is used to control the FHR and FHR beat-to-beat variability displayed on the chart recorder and the seven segment display when the FBPM is executed in the EDIT mode. It is important to note that the rate running average, per se, is not displayed.

A special, EDIT/NO EDIT, toggle switch, located on the back of the monitor chassis, is used to control the FBPM routine output. This switch modifies the rate and variability values displayed on the chart recorder and the seven segment display in the following way. If the switch is off, NO EDIT 229, all FHR and VAR values computed are displayed on both the chart recorder and the seven segment LED's 239. Rates greater than 210 bpm, however, are reported as 210 bpm, and rates less than 30 bpm are reported as 30 bpm, and variabilities greater than 20 bpm are reported as 20 bpm. If the edit switch is on (EDIT), the fetal rate running average is used to determine whether the results are to be reported at all. Each time a fetal detection occurs and the fetal rate is calculated, the rate is compared to the fetal rate running average. If the difference between the two is greater than 30 bpm 231, or the FHR variability calculated 235 is greater than 20 bpm 237, then the rate for that interval, and the variability for the next two intervals are not reported on the chart recorder 233 or the seven segment display. That is, no rate or variability is reported on the chart recorder and the last valid FHR and FHR variability reported on the seven-segment display is not updated.

The FBPM routine requires an estimate of the noise level obtained from the SQR array data. A new estimate of this noise level is calculated every 500 ms in the following way. The FBPM routine excises a 60 ms window centered about every fetal peak maximum that is detected in the SQR array 241. At the end of the FBPM routine, the only data remaining in array SQR is considered to be noise. The next procedure, FIND_NOISE 177 (FLOWCHART - I) is executed immediately after FBPM to estimate the noise level of the original SQR data based on the remaining data in SQR after fetal peaks are excised by the FBPM routine.

f. FIND_NOISE 177, (FLOWCHART - I)

This procedure finds the maximum value in SQR and places the value in a buffer of the last 8 noise values found in the same way. The oldest value is thrown out and the average of this Noise Peak array is calculated. This average is stored as the variable NOISE, which is subsequently used in the next execution of FBPM. See FIG. 10 for a flow chart of the FBPM procedure.

g. MBPM (Maternal Beats Per Minute Routine 165, FLOWCHART - I)

This procedure peak detects the thoracic ECG data in T2 and converts the maternal R-R intervals into instantaneous maternal heart rate, which is stored in the SEV_SEG array and later sent to the seven segment MHR display.

3. STORE_ARRAYS 179 (FLOWCHART - I)

In the main routine, signal processing is completed once the FBPM routine finishes its execution. At this point in the main routine, the type of chart recorder output must be determined, and the data to be output must be placed in the output buffer in order to be accessed by the I/O interrupt service routine, SAMPLE_INT 155 (FLOWCHART - I). A rotary switch on the monitor's front panel is used for chart recorder output mode control. The four modes are:

FECG Mode—Two channel output. 50mm width per channel. Chart speed is 25 mm/s. First channel is A1, abdominal data. Second channel is R1NEW, cancelled abdominal data.

Mode No. 1—Two channel output. 50mm width per channel. Chart speed is 25mm/s. First channel is R1NEW, canceled abdominal data. Second channel is RMFNEW, matched filter output.

Mode. No. 2—Four channel output. 20mm width per channel. Chart speed is 25 mm/s. First channel is SQR, squared output. Second channel is Noise data from SQR array. Third channel is the fetal threshold level. Fourth channel is BPM.

Mode FHR—Three channel output. First channel is 60mm wide. Second and third channel use a common 40mm width grid. First channel is BPM. Second channel is VAR. Third channel will be Uterine Activity.

The subroutine, STORE_ARRAYS, reads this switch, and, if it has been changed from its last setting, the system reinitializes the chart recorder for the new operation mode. The chart recorder mode determines what output data is loaded into the output buffer. The first four channels of the output buffer are reserved for chart recorder output. The data is scaled and offset based on the channel width, type of data, and the setting of the scaling switches on the monitor's back panel. The next two channels of the output buffer are loaded with data to be used for CRT output. This data comes from the arrays, A1 and R1NEW. The data from this channel is available for output on the CRT by SAMPLE_INT. The last channel of the output buffer is loaded with data from the SEV_SEG array. This data is sent to the seven segment display by SAMPLE_INT.

The output to the CRT is toggled between two different types of outputs. A push button, labeled Abdominal/Fetal, is used to toggle between the two CRT outputs. The default output, A1, is the Abdominal output, and R1NEW, the Fetal output, is the second output. The CRT data is time aligned with the chart recorder data. The Fetal output is the residual fetal signal from the cancellation algorithm, and is valuable as an indicator of the cancellation routine's effectiveness.

The detection and debounce control of the front panel push buttons is done by the push-button interrupt service routine, KEY_INT 157 (FLOWCHART - I), every 100ms. This routine maintains a status byte with information about the control state of all devices controlled by the push buttons. The push buttons are actually read every 2.0 ms by SAMPLE_INT. A flag bit is set for each push button that is depressed. The flag bits are read and cleared, and the push buttons that have been depressed are debounced by KEY_INT. The function controlled by the push buttons are listed below. All functions not already described are executed in the push-button interrupt service routine.

1. Record Button—This control starts and stops the chart recorder. The chart lamp is on when the recorder status bit is on.

2. Fetal/Abdominal Button—This control was described above. No indicator is used.

3. Freeze/Scan Button—This push-button controls the CRT hardware. The default state (Scan) allows the CRT to constantly display new data. The other state freezes the display. No indicator is used.

4. Restart Button—This push-button state is read by the section of code in the main routine that controls the execution of the MFSU, SQUARE and FBPM routines. No indicator is used.

5. Test Button—This push-button status is used to toggle the type of output displayed on the seven segment displays and the CRT. At the beginning of the main routine this status bit is polled to determine if regular Rate, Variability, etc., data is displayed on the seven segments or if diagnostic data is displayed. The test lamp is turned on if diagnostics are being displayed. When the test status is on all eight channels of raw data can be viewed on the CRT and can be sequentially selected by depression of the Abdom/Fetal push button. Otherwise the standard CRT data is displayed.

6. Uterine Activity Button—This push-button function is used to set the baseline of the uterine activity signal to a baseline level of ten mm Hg.

The tables below illustrate the method of determining a suitable Fetal Window to be used by the MFLTR procedure. Table - I lists the data (in digital format) corresponding to the fetal ECG signals shown in FIG. 8. Ten sets of thirty Fetal Window Coefficients are listed that correspond to the ten (10) Fetal Windows shown in the lower tracing of FIG. 8.

Table - II lists normalized fetal ECG correlation coefficients in which the autocorrelation coefficients, along the diagonal, are set equal to 1.0. In each Fetal window set the largest two cross correlation coefficients are underlined. The average of these two cross correlation coefficients is then listed in the right hand column. The algorithm selects the highest average which is also underlined here.

In this example, the STARTUP procedure selects Fetal Window number 4 as the matched filter window from this data set.

TABLE - I

TABLE - II

While the invention has been described with reference to specific embodiments, modifications and variations of the invention may be constructed without departing from the scope of the invention. The scope of the invention is defined in the following claims.

We claim:

1. A noninvasive -instantaneous fetal heart rate and beat-to-beat variability monitor comprising maternal abdominal electrode means adopted for connecting to an abdomen and for supplying inputs of maternal abdominal ECG and fetal ECG signals, thoracic electrode means for supplying maternal thoracic ECG signals, abdominal input means connected to the abdominal electrode means and thoracic input means connected to the thoracic electrode means for receiving the inputs, multiplexing means connected to the input means for multiplexing the inputs, analog-to-digital converter means connected to the multiplexing means for converting analog inputs of ECG signals from the electrode means to digital signals, processor means connected to the converter means for processing the signals, EPROM module means connected to the processor means for controlling the processor means to employ the thoracic and maternal abdominal ECG signals and to provide said fetal ECG signals, signal enhancement means for enhancing said fetal ECG signals, fetal ECG detection means for detecting fetal ECG signals, conversion means connected to the detection means for converting a continuous fetal ECG signal into instantaneous fetal heart rate and beat-to-beat fetal heart rate variability signals, output means connected to the processor means, the output means comprising display means for displaying instantaneous fetal heart rate and beat-to-beat variability, scan means connected to said output means for supplying scan signals, freeze means connected to the scan means for freezing the scan signals, selector means connected to the scan and freeze means for selecting scan or freeze signals and CRT screen means connected to the selector means for supplying the scan or freeze signals selected by the selector means of the abdominal ECG signal or fetal ECG signal, printer means connected to the output means for printing instantaneous fetal heart rate and beat-to-beat variability and digital display means connected to the output means for digitally displaying instantaneous fetal heart rate and beat-to-beat variability.

2. A noninvasive instantaneous fetal heart rate and beat-to-beat variability monitor apparatus comprising abdominal signal input means for supplying maternal abdominal ECG and fetal ECG signals, thoracic signal input means for supplying maternal thoracic ECG signals, analog signal conditioning means for multiplexing the signals, analog-to-digital converter means connected to the thoracic and abdominal signal input means for converting signals from the conditioning means to thoracic and abdominal digital input signals, buffer means for buffering the digital input signals, processor means connected to the buffer means for processing the digital signals, control means connected to the processor means for controlling the processor means for employing the thoracic and abdominal signals for adaptively canceling maternal abdominal signals and enhancement means connected to the processor means for enhancing fetal ECG signals, fetal ECG detection means for detecting fetal ECG signals, conversion means connected to the detection means for converting a continuous fetal ECG signal into instantaneous fetal heart rate and beat-to-beat fetal heart rate variability signals, output means further connected to the processor means, the output means comprising abdominal input signal means and instantaneous fetal heart rate output signal means, scan means connected to the output means for supplying scan signals, freeze means connected to the scan means for freezing the scan signals, and CRT screen means connected to the scan means for displaying the scan or freeze signals.

3. The apparatus of claim 2 wherein the output means further comprises instantaneous fetal heart rate output means and beat-to-beat variability signal means.

4. The apparatus of claim 3 further comprising seven-segment digital display means connected to the instantaneous fetal heart rate output means and beat-to-beat variability means for digitally displaying instantaneous fetal heart rate and beat-to-beat variability.

5. The apparatus of claim 3 further comprising printer means connected to the output means for printing parallel graphic displays.

6. The noninvasive instantaneous fetal heart rate monitor apparatus of claim 5 further comprising uterine activity input means for receiving electrical signals of uterine activity, the uterine activity input means being connected to the analog signal conditioning means and wherein the output means and the seven-segment digital display means further comprise maternal heart rate display means and uterine activity display means.

7. A noninvasive fetal heart rate monitoring method comprising placing maternal thoracic and abdominal electrodes on a maternal abdomen and chest, connecting said maternal abdominal electrodes to an input and supplying analog maternal abdominal ECG and fetal ECG signals as inputs, connecting said thoracic electrodes to an input and supplying analog maternal thoracic ECG signals as inputs, conditioning analog ECG signals from all the electrods and inputs and converting the conditioned analog signals to digital ECG signals, processing the digital signals, controlling the processing and employing the thoracic and maternal abdominal ECG digital signals, adaptively cancelling the maternal abdominal ECG signals and providing instantaneous fetal ECG signals, enhancing the fetal signals, providing abdominal ECG output signals and providing instantaneous fetal ECG output signals, selecting one of the output signals, supplying scane signals of the selected output signals, freezing the scan signals, supplying the selected scan or freeze signals to a CRT screen and displaying the abdominal ECG or fetal ECG signals, moving the electrodes until the desired signals appear.

8. The method of claim 7 further including providing instantaneous fetal heart rate output and beat-to-beat variability outputs and illuminating digital displays of instantaneous fetal heart rate and beat-to-beat variability.

9. The method of claim 8 further comprising printing parallel graphic displays of instantaneous fetal heart rate signals and beat-to-beat variability.

10. The noninvasive instantaneous fetal heart rate monitoring method of claim 7 further comprising receiving electrical signals of uterine activity, connecting the uterine activity signals to an input, conditioning the uterine activity signals, converting the signals in analog-to-digital converter means, and wherein the displaying further comprises displaying maternal heart rate and uterine activity.

11. A noninvasive electrocardiographic method of real time signal processing for obtaining instantaneous fetal heart rate and fetal heart rate beat-to-beat variability indications comprising creating sampling rate signals with a clock, collecting data from ECG electrodes on multiple electrocardiographic data acquisition channels according to the sampling rate signals, separately storing the collected data from the multiple channels, processing the stored data adaptively cancelling maternal elecgtrocardiographic data in contiguous data windows and producing output signals, sending the output signals to a CRT display, and sending the output signals to a fetal heart rate and fetal heart rate beat-to-beat variability chart recorder and numerical display.

12. The method of claim 11 wherein the creating sampling rate signals comprises creating sampling rate signals independently of the processing.

13. The method of claim 11 further comprising conditioning the collected data and multiplexing the conditioned data.

14. The method of claim 13 further comprising multiplexing the conditioned data and converting the multiplexed data to digital data.

15. The method of claim 11 wherein the collecting data comprises inputting thoracic signals from a mother and abdominal signals from the mother and wherein the processing comprises processing the thoracic signals and generating continuously in real time an orthogonal vector set of the mother's ECG and wherein the processing further includes using the orthogonal set for removing maternal ECG and noise from the abdominal signal, leaving fetal ECG complexes and other noise.

16. The method of claim 15 wherein the processing comprises executing a start-up routine automatically after predetermined data are collected or manually by pressing a restart push button and finding a fetal ECG time template to match the fetal complexes and using a result for calculating an initial threshold for fetal detecting and for calculating initial noise level in the fetal complexes.

17. The method of claim 15 further comprising increasing fetal signal-to-noise ratio by using a pattern recognition algorithm using a template and applying a matched filter to the result array of the fetal ECG complexes and noise.

18. The method of claim 15 further comprising squaring positive values of a matched filter output for further improving signal-to-noise ratio.

19. The method of claim 18 further comprising detecting intervals between peaks of fetal ECG complexes and converting the intervals into instantaneous fetal heart rate and fetal heart rate beat-to-beat variability.

20. The method of claim 19 further comprising placing the results of fetal heart rate and fetal heart rate variability into arrays and time aligning those arrays with other output arrays.

21. The method of claim 20 further comprising displaying the fetal heart rate and fetal heart rate variability on the chart recorder and on seven-segment displays.

22. The method of claim 21 further comprising measuring intervals between peak detections of maternal ECG thoracic signals and determining maternal heart rate from the measuring and displaying maternal heart rate on the seven-segment display.

23. The method of claim 20 wherein the processing further comprises using a start-up procedure to find a fetal ECG template to be used for a matched filter algorithm, using the start-up procedure and calculating an initial threshold level for peak detection of squared output and using the start-up procedure and finding an initial value of noise level and squared output.

24. The method of claim 23 further comprising extracting points of said fetal ECG template and storing the points by first collecting about twelve seconds of raw data from a thoracic channel and from an abdominal channel, placing the collected data in a thoracic array and an abdominal array, excising maternal complexes from the abdominal array by peak detecting from the thoracic array using a threshold that is a predetermined percent of maximum data amplitude in the thoracic array and excising the corresponding data points in the abdominal array which are centered around each detected maternal complex, thereby producing an excised data including only fetal complexes and noise.

25. The method of claim 24 further comprising displaying fetal complexes on an ECG and moving electrodes on a patient until fetal complexes are observed.

26. The method of claim 24 further comprising peak detecting the fetal complexes using a threshold that is a percent of maximum excursion of the excised data in the abdominal array and storing centered windows for each fetal complex detected and thereby producing an $N \times N$ array of N potential fetal ECG complexes.

27. The method of claim 26 further comprising checking for a number of stored fetal peaks and, upon finding that number, calculating an $N \times N$ array of normalized correlation coefficients and averaging two largest normalized cross correlation coefficients for each fetal peak, selecting the fetal peak with the largest average as the matched filter fetal window when an average correlation coefficient is greater than a predetermined value and terminating the storage of the coefficients in the template.

28. The method of claim 27 further comprising cancelling the fetal window when the largest average correlation coefficient is less than a predetermined value and restarting the start-up routine.

29. The method of claim 11 further comprising displaying maternal ECG signals and instantaneous fetal heart beat signals on a CRT display and relocating electrodes on a subject until desirable signals are displayed.

30. A noninvasive electrocardiographic method of real time digital signal processing for obtaining and displaying instantaneous fetal heart rate and fetal heart rate beat-to-beat variability indications comprising collecting analog signals from thoracic and abdominal electrodes, conditioning the collected signals, converting the conditioned analog signals to digital data, providing said digital data to a processor, processing and cancelling in continuous cancellation windows all data common to the abdominal data and thoracic data, enhancing noncommon data as a fetal ECG signal, producing therefrom an instantaneous fetal heart rate signal, storing fetal heart rate signals and comparing stored fetal heart rate signals to current fetal heart rate signals and producing therefrom an indication of fetal heart rate beat-to-beat variability, and displaying the instantaneous fetal heart rate and beat-to-beat variability.

31. The method of claim 30 further comprising storing digital data from the analog-to-digital conversion and sampling the stored data at a sampling rate.

32. The method of claim 31 further comprising sampling the digital data in bursts of about 120 $\mu$sec.

33. The method of claim 30 wherein the cancellation occurs in contiguous cancellation windows of at least about 500 msec and wherein the cancellation windows are selected independent of maternal ECG complexes wherein the windows may include all, part, none or more than one maternal complex.

34. A noninvasive electrocardiographic method of real time digital signal processing for obtaining and displaying instantaneous fetal heart rate and fetal heart rate beat-to-beat variability indications comprising placing thoracic and abdominal electrodes in contact with a patient collecting analog signals from the thoracic and abdominal electrodes, conditioning the collected signals, converting the conditioned analog signals to digital data, providing said digital data to a processor, processing and cancelling all data common to the abdominal data, enhancing noncommon data as a fetal ECG signal, and producing therefrom an instantaneous fetal heart rate signal, storing fetal heart rate signals and comparing stored fetal heart rate signals to current fetal heart rate signals and producing therefrom an indication of fetal heart rate beat-to-beat variability, and displaying the instantaneous fetal heart rate and beat-to-beat variability, further comprising placing electrodes on a maternal chest and placing an electrode on a maternal abdomen before collecting signals from all of the electrodes, and watching displays of the processed data on a CRT screen, and comparing the displays on the screen with predetermined desired displays, moving and relocating the abdominal electrode and observing the CRT screen until the desired display is reached.

35. The method of claim 34 further comprising placing two maternal abdominal electrodes, placing the first maternal abdominal electrode near a fetal head and placing the second maternal abdominal electrode near fetal buttocks.

36. The method of claim 34 further comprising placing a first thoracic electrode on a left side of a mid-axial line, placing another thoracic electrode below a sternal notch and placing two additional thoracic electrodes on opposite mid-clavicles.

37. The method of claim 34 further comprising multiplexing the collected signals from the electrodes and providing multiplexed signals to a converter, converting the multiplexed signals to digital data, storing the digital data in a RAM and further comprising sampling the digital data in the RAM as synchronized by a sample rate clock.

38. The method of claim 37 further comprising buffering the sampled data and transferring the buffered data to the processor.

39. The method of claim 37 wherein collecting, multiplexing, storing and sampling are under peripheral hardware control.

40. A method of continuously accurately and noninvasively measuring and indicating instantaneous fetal heart rate and beat-to-beat variability in real time comprising receiving maternal ECG thoracic data and receiving maternal and fetal abdominal ECG data, collecting the received data and periodically repetitively sampling the received and collected data, cancelling in contiguous windows all data which is common to the maternal thoracic ECG data and the abdominal maternal and fetal ECG data and leaving fetal ECG signals, storing and presenting the fetal ECG signals, enhancing the fetal ECG signals, and measuring time intervals between the enhanced fetal ECG signals and presenting indications of the time intervals as instantaneous heart rate, measuring change in heart rate and presenting the measured change as beat-to-beat variability.

41. The method of claim 40 wherein the receiving and collecting occurs continuously and the collecting occurs repetitively under the control of an independent clock.

42. The method of claim 40 wherein the sampling of collected data occurs in a burst at a relatively fast rate as compared to the collecting.

43. The method of claim 40 wherein the sampling occurs in a burst format.

44. The method of claim 40 wherein the collecting step comprises collecting ECG signals from thoracic and abdominal electrodes, presenting the collected signals on an oscilloscope and moving an abdominal electrode until a desired signal is displayed.

45. A method of measuring intervals between fetal heart beats continuously in real time by continuously accurately and noninvasively collecting ECG signals from maternal thoracic and abdominal electrodes, amplifying the signals, filtering the signals and multiplexing the signals, converting the multiplexed signals to digital signals, storing the digital signals, periodically sampling the stored digital signals in signal bursts according to control clock pulses, providing the signal bursts to bus buffers, providing the signal bursts from the bus buffers to a processor, cancelling common signals from the abdominal and thoracic electrodes of the bursts with the processor, enhancing resultant signals as indicator signals and providing the indicator signals from the processor.

46. The method of claim 45 wherein the storing further comprises collecting digital signals in a RAM buffer and controlling the collecting with clocking signals independently of the processor.

47. The method of claim 46 wherein the sampling further comprises sampling the stored digital signals from the RAM buffer at a relatively high rate and over a relatively short period as compared to the collecting, as controlled by the clocking signals.

48. The method of claim 47 wherein the sampling comprises sampling signal bursts of relatively short duration compared to intervals of the sampling rate as controlled by the clocking signals independently of the processor.

49. The method of claim 47 wherein the storing and sampling and providing signal bursts are controlled independently of the processor.

50. The method of claim 45 wherein the providing indicator signals step comprises presenting an indication of ECG signals and further comprising moving material electrodes until a desired presentation is achieved.

51. The method of claim 45 wherein the processor processes the signal bursts; by moving signal bursts from input buffers into arrays and removing maternal ECG signals from each of the arrays by performing a subroutine for determining maternal beats per minute by detecting peaks, and converting intervals between detections into instantaneous maternal heart rate and placing maternal heart rate values into a seven-segment array and wherein the cancelling comprises cancelling the maternal thoracic signal from the abdominal signal by orthogonalizing signals and subsequently adaptively cancelling the maternal signal from the abdominal signal and placing the results in a result array.

52. The method of claim 51 further comprising performing a matched filter startup comprising moving thoracic and abdominal data from a input buffer to thoracic and abdominal arrays, excising maternal complexes from the abdominal array using the thoracic array for detection, detecting threshold as a percent of maximum excursion in the thoracic array, excising windows, detecting potential fetal peaks in the abdominal array using a fetal threshold that is a percent of maximum excursion of the abdominal array, storing a number of peaks in a fetal peak array, calculating normalized cross correlation coefficients for all potential fetal peaks, averaging the largest correlation coefficients for each peak and storing the fetal peak with the largest average as the matched filter fetal window, determining an initial fetal threshold by calculating autocorrelation of the fetal window and storing a percent of a square of the autocorrelation as the square threshold, taking data from the abdominal array and matching it with a new fetal window, squaring positive values of that data and then excising windows from the squared results to remove fetal peaks and storing the maximum of the remaining data as initial noise.

53. The method of claim 52 further comprising performing a matched filter process on data in the result array using the filter window coefficients from the matched filter startup routine and placing a output in an output array thereby increasing fetal signal-to-noise ratio, squaring positive data in the output and placing the squared result in a squared array, thus increasing fetal signal-to-noise ratio for peak detection.

54. The method of claim 53 further comprising establishing fetal beats per minute by detecting peak data in the squared array using squared threshold starting at the beginning of the array, finding the peak maximum if detection occurs before reaching an end of the array, filling a beats per minute array and variability arrays with a last good rate and variability when peak maximum is still in the squared array, finding an average peak value based on maximum of a last number of peaks detected and calculating a new squared threshold, calculating a new rate by finding a period in predetermined intervals since the last detection and converting the interval into beats per minute, calculating a new average rate from a last number of good intervals and determining if the new average rate is within 30 beats per minute of the average, if that is true, calculating a new variability by finding change in rate from the last good rate, placing the new good rate and variability in a digital display and a chart recorder and detecting peaks using the new threshold starting after the last detailed peak maximum, and upon reaching the end of the squared array filling remainder of the beats per minute and variability arrays with the last good rate and variability.

55. The method of claim 53 further comprising finding noise by excising windows from the squared array for each fetal detection, finding maximum of remaining data as a noise peak, calculating noise as a average of a last number of noise peaks.

56. The method of claim 55 further comprising moving data from the data arrays into an output buffer and moving data from the output buffer into a chart recorder output and into a CRT output.

57. A noninvasive fetal electrocardiographic method comprising collecting maternal electrocardiographic data, determining fetal complexes in the data, executing a start-up routine automatically after predetermined data are collected or manually by pressing a restart push button and finding a fetal ECG time template to match the fetal complexes and using a result for calculating an initial threshold for fetal detecting and for calculating initial noise level in the fetal complexes.

58. The method of claim 57 further comprising peak detecting the fetal complexes using a threshold that is a percent of maximum excursion of excised data in an abdominal array and storing centered windows for each fetal complex detected and thereby producing an $N \times N$ array of N potential fetal ECG complexes.

59. The method of claim 57 further comprising checking for a number of stored fetal peaks and, upon finding that number, calculating an $N \times N$ array of normalized correlation coefficients and averaging two largest normalized cross correlation coefficients for each fetal peak, selecting the fetal peak with the largest average as the matched filter fetal window when average correlation coefficient is greater than a predetermined value and terminating the storage of the coefficients in the template.

60. The method of claim 57 further comprising cancelling a fetal window when a largest average correlation coefficient is less than a predetermined value and restarting the start-up routine.

61. A noninvasive fetal electrocardiographic method comprising collecting thoracic signals from a mother and abdominal signals from the mother and processing in contiguous windows the thoracic signals and generating continuously in real time an orthogonal vector set of the mother's ECG and using in the windows the orthogonal set for removing maternal ECG and noise from the abdominal signal, leaving fetal ECG complexes.

62. The method of claim 61 further comprising increasing fetal signal-to-noise ratio by using a pattern recognition algorithm using a template and applying a matched filter to a result array of the fetal ECG complexes and noise.

63. The method of claim 61 further comprising squaring positive values of a matched filter output for further improving signal-to-noise ratio.

64. The method of claim 61 further comprising detecting intervals between peaks of fetal ECG complexes and converting the intervals into instantaneous fetal heart rate and fetal heart rate beat-to-beat variability.

65. A noninvasive fetal electrocardiographic method comprising determining fetal heart rate and beat-to-beat variability from noninvasive maternal measurements and displaying the fetal heart rate and fetal heart rate variability on a chart recorder and on seven-segment displays.

66. The method of claim 65 further comprising measuring intervals between peak detections of maternal ECG thoracic signals and determining maternal heart rate from measuring and displaying maternal heart rate on the seven-segment display.

67. The method of claim 65 further comprising displaying maternal ECG signals and instantaneous fetal heart beat signals on a CRT and relocating electrodes on a subject until desirable signals are displayed.

68. The method of claim 65 including processing using a start-up procedure to find a fetal ECG template to be used for a matched filter algorithm, using the start-up procedure and calculating an initial threshold level for peak detection of squared output and using the start-up procedure and finding an initial value of noise level and squared output.

* * * * *